(12) United States Patent
Caron et al.

(10) Patent No.: US 9,139,638 B2
(45) Date of Patent: Sep. 22, 2015

(54) MOUSE MODEL OF CHOLINERGIC DYSFUNCTION TO EVALUATE COGNITIVE ENHANCERS AND DRUGS THAT IMPROVE MYASTHENIA

(75) Inventors: Marc G. Caron, Hillsborough, NC (US); Vania F. Prado, Belo Horizonte (BR); Marco A. Prado, Belo Horizonte (BR); Raul Gainetdinov, Chapel Hill, NC (US); Grace S. Pereira, Belo Horizonte (BR); Braulio M. Castro, Belo Horizonte (BR); Cristina M. Silva, Belo Horizonte (BR); Ivan A. Izquierdo, Porto Alegre (BR)

(73) Assignees: Duke University, Durham, NC (US); Universidade Federal de Minas Gerais, Belo Horizonte (BR)

( * ) Notice: Subject to any disclaimer, the term of this patent is extended or adjusted under 35 U.S.C. 154(b) by 1165 days.

(21) Appl. No.: 11/842,406

(22) Filed: Aug. 21, 2007

(65) Prior Publication Data
US 2008/0052785 A1 Feb. 28, 2008

Related U.S. Application Data

(60) Provisional application No. 60/838,979, filed on Aug. 21, 2006.

(51) Int. Cl.
*A01K 67/027* (2006.01)
*C07K 14/705* (2006.01)
*C12N 15/85* (2006.01)

(52) U.S. Cl.
CPC ....... *C07K 14/70571* (2013.01); *A01K 67/0276* (2013.01); *C12N 15/8509* (2013.01); *A01K 2217/075* (2013.01); *A01K 2217/20* (2013.01); *A01K 2227/105* (2013.01); *A01K 2267/0356* (2013.01); *C12N 2800/30* (2013.01)

(58) Field of Classification Search
USPC .................................. 800/18, 8, 3; 435/325
See application file for complete search history.

(56) References Cited

U.S. PATENT DOCUMENTS 7,301,068 B2 11/2007 Takai et al.
7,446,239 B2 11/2008 Pulst

OTHER PUBLICATIONS

Schutz (J. Neurochem. 2003, vol. 87, p. 1174-1183).*
Nangle (British Journal of Pharm., Jun. 2006, vol. 148, p. 423-433).*
Prado (Neuron, Sep. 2006, vol. 51, p. 601-612) t.*
Guidine (Neurosci. Letters, 2008, vol. 436, p. 201-204).*
MGI website, see Mammalian Phenotype Browser for "progressive muscle weakness", 2009.*
MGI website, see Mammalian Phenotype Browser for "muscle weakness", 2009.*
MGI website Mammalian Phenotype Browser for "abnormal posture", 2009.*
MGI website, "Mammalian Phenotype Browser" for abnormal object recognition memory, 2009.*
de Castro (Mol. and Cellular Biology, Oct. 2009, vol. 29, No. 19, p. 5238-5250).*
Efange (Neurobiology of Aging, 1997, vol. 18, No. 4, p. 407-413).*
Lara (Mol. and Cellular Biology, Apr. 2010, vol. 30, No. 7, p. 1746-1756).*
PCT International Search Report and Written Opinion, PCT/US07/18499, mailed Dec. 18, 2007.
MGI website, Gene detail for Slc18a3, Nov. 26, 2007, 2 pages.
Prado V F, et al. Mice deficient for the vesicular acetylcholine transporter are myasthenic and have deficits in object and social recognition. Neuron (Sep. 7, 2006) vol. 51, pp. 1-12.
Ferreira L T, et al. Structural requirements for steady-state localization of the vesicular acetylcholine transporter. Journal of Neurochemistry (2005) vol. 94, pp. 957-969.
Csernansky J G, et al. Cholinesterase inhibitors ameliorate behavioral deficits induced by MK-801 in mice. Neuropsychopharmacology (2005) vol. 30, pp. 2135-2143.
Croft B G, et al. Normal biogenesis and cycling of empty synaptic vesicles in dopamine neurons of vesicular monoamine transporter 2 knockout mice. Molecular Biology of the Cell (Jan. 2005) vol. 15, pp. 306-315.
Ferguson S M, et al. Lethal impairment of cholinergic neurotransmission in hemicholinium-3-sensitive choline transporter knockout mice. PNAS (Jun. 8, 2004) vol. 101, No. 23, pp. 8762-8767.
Erickson J D, et al. Functional identification of a vesicular acetylcholine transporter and its expression from a "cholinergic" gene locus. The Journal of Biological Chemistry (Sep. 2, 1994) vol. 269, No. 35, pp. 21929-21932.
Bejanin S, et al. A unique gene organization for two cholinergic markers, choline acetyltransferase and a putative vesicular transporter of acetylcholine. The Journal of Biological Chemistry (Sep. 2, 1994) vol. 269, No. 35, pp. 21944-21947.
Efange SMN et al. Vesicular acetylcholine transporter density and Alzheimer's disease. Neurobiology of Aging. 1997; 18(4): 407-413.
Bartus RT. On neurodegenerative diseases, models and treatment strategies: lesions learned and lessons forgotten a generation following the cholinergic hypothesis. Experimental Neurology. 2000; 163: 495-529.

(Continued)

*Primary Examiner* — Michael Wilson
(74) *Attorney, Agent, or Firm* — Myers Bigel Sibley & Sajovec, P.A.

(57) ABSTRACT

Recombinant non-human mammals having reduced or no expression of vesicular acetylcholine transporter protein (VAChT) as compared to the corresponding wild-type mammal are provided. The mammal may have, e.g., impaired performance in object and social recognition and/or impaired neuromuscular performance and/or alterations in autonomic nervous system function as compared to the corresponding wild-type mammal. Methods of screening a compound for cholinergic activity or activity in treating a cholinergic neurotransmission disorder are also provided. In addition, a cell such as a nerve cell isolated from a mammal as described herein is provided, along with cell cultures, which are useful in vitro for screening the activity of candidate compounds for their effect on cholinergic neurotransmission, and for their activity in treating cholinergic neurotransmission disorders.

17 Claims, 12 Drawing Sheets

(56) References Cited

OTHER PUBLICATIONS

Auld DS et al. Alzheimer's disease and the basal forebrain cholinergic system: relations to β-amyloid peptides, cognition, and treatment strategies. Progress in Neurobiology. 2002; 68: 209-245.

Terry AV, Jr. et al. The cholinergic hypothesis of age and Alzheimer's disease-related cognitive deficits: recent challenges and their implications for novel drug development. The Journal of Pharmacology and Experimental Therapeutics. 2003; 306(3): 821-827.

Lee Ach et al. Associative and recognition memory for novel objects in dementia: implications for diagnosis. European Journal of Neuroscience. 2003; 18: 1660-1670.

Smith R et al. Cholinergic neuronal defect without cell loss in Huntington's disease. Human Molecular Genetics. 2006; 15(21): 3119-3131.

De Castro BM et al. Reduced expression of the vesicular acetylcholine transporter causes learning deficits in mice. Genes, Brain and Behavior. Sep. 6, 2008 (Epub ahead of print): 1-13.

Whitehouse et al. "Alzheimer's Disease and Senile Dementia: Loss of Neurons in the Basal Forebrain." Science, vol. 215 4537: 1237-1239 (1982).

Kuhl et al. "In Vivo Mapping of Cholinergic Terminals in Normal Aging, Alzheimer's Disease, and Parkinson's Disease." Ann. Neurol. 40:399-410 (1996).

Finch et al. "Part Four. Growth, Development and Differentiation 30. Biochemistry of Aging: Neurotransmitters and Receptors." in *Basic Neurochemistry* (George J. Siegel et al., eds., 1999).

Taylor et al. "Part Two. Intercellular Signaling 11. Acetylcholine. Synthesis, Storage and Release of Acetcholine." in *Basic Neurochemistry*, (George J. Siegel et al., eds., 1999).

Blusztajn et al. "The Cholinergic Neuronal Phenotype in Alzheimer's Disease." Metabolic Brain Disease 15(1):45-64 (2000).

"Quantal transmission at neuromuscular synapses," in *Neuroscience*, 2nd edition, Part I: Neural Signaling (Purves et al., eds., 2001).

Ohno et al. "Choline acetyltransferase mutations cause myasthenic syndrome associated with episodic apnea in humans." Proc. Nat. Acad. Sci. 98(4):2017-2022 (2001).

Bravo et al. "Microscopic kinetics and structure-function analysis in the vesicular acetylcholine transporter." Neurochemistry International 41: 285-289 (2002).

Suzuki et al. Cholinergic vescicular transporters in progressive supranuclear palsy. Neurology 58:1013-1018 (2002).

Terry, Jr. et al. "The Cholinergic Hypothesis of Age and Alzheimer's Disease-Related Cognitive Deficits: Recent Challenges and Their Implications for Novel Drug Development." J. Pharmacology and Experimental Therapeutics 306:821-827 (2003).

Harper. "Congenital Myasthenic Syndromes." Seminars in Neurology 24(1):111-123 (2004).

Lahiri et al. "Rationale for the Development of Cholinesterase Inhibitors as Anti-Alzheimer Agents." Current Pharmaceutical Design 10:3111-3119 (2004).

Bales et al. "Cholinergic dysfunction in a mouse model of Alzheimer disease is reversed by an anti-Aβ antibody." The Journal of Clinical Investigation 116(3): 825-832 Mar. 2006.

Terry, Jr. "Chapter 2: Muscarinic Receptor Antagonists in Rats." in *Animal Models of Cognitive Impairment* (Levin et al., eds., 2006).

Zhang. "Cholinergic Receptor Knockout Mice." in *Animal Models of Cognitive Impairment*, (Levin et al., eds., 2006).

Edwards. "The Neurtransmitter Cycle and Quantal Size." Neuron 55:835-858 Sep. 2007.

Kinali et al. "Congenital Myasthenic Syndromes in childhood: Diagnostic and management challenges." Journal of Neuroimmunolog 201-202:Jun. 6-12, 2008.

Mazère et al. "In vivo SPECT imaging of vesicular acetylcholine transporter using [$^{123}$I]-IBVM in early Alzheimer's disease." NeuroImage 40:280-288 (2008).

Prado et al. "VAChT." UCSD-Nature Molecule Pages, Published online: May 16, 2008 | doi:10.1038/mp.a002796.01.

Bryan et al. "Chapter 1: Transgenic Mouse Models of Alzheimer's Disease: Behavioral Testing and Considerations." in *Methods of Behavior Analysis in Neuroscience*, (Jerry J. Buccafusco, ed., 2009).

Curzon et al. "Chapter 8: The Behavioral Assessment of Sensorimotor Processes in the Mouse: Acoutic Startle, Sensory Gating, Locomotor Activity, Rotarod, and Beam Walking." in *Methods of Behavior Analysis in Neuroscience*, (Jerr J. Buccafusco, ed., 2009).

Muth et al. "Mild Cognitive Impairment in the Elderly is Associated with Volume Loss of the Cholinergic Basal Forebrain Region." J. Biol. Psychiatry (Article in Press) (2009).

Alzheimer'S Association "10 Signs of Alzheimer's." avaliable at: http://www.alz.org/alzheimers_disease_10_signs_of_alzheimers.asp, downloaded Jun. 19, 2009.

Ferguson JN et al. Social amnesia in mice lacking the oxytocin gene. Nature Genetics. Jul. 2000; 25: 284-288.

Lara A et al. Dysautonomia due to reduced cholinergic neurotransmission causes cardiac remodeling and heart failure. MCB Accepts. Feb. 1, 2010; 50 pp.

Alzheimer's Disease Guide. WebMD. Downloaded May 17, 2010: 2 pp.

Crawley JN. What's wrong with my mouse? Behavioral phenotyping of transgenic and knockout mice, 2nd ed. Chapter 4, Motor Functions. Wiley Interscience. 2007, pp. 63-75.

Crawley JN. What's wrong with my mouse? Behavioral phenotyping of transgenic and knockout mice, 2nd ed. Chapter 6, Learning and Memory. Wiley Interscience. 2007, pp. 111-133, 144-151.

Crawley JN. What's wrong with my mouse? Behavioral phenotyping of transgenic and knockout mice, 2nd ed. Chaster 9, Social Behaviors. Wiley Interscience. 2007, pp. 207-223.

PubMed Health—Pyridostigmine. National Center for Biotechnology Information. Obtained Oct. 15, 2010, 3 pp.

PubMed Health—Galantamine. National Center for Biotechnology Information. Obtained Oct. 15, 2010, 5 pp.

End-plate potential. Wikipedia. Obtained Oct. 14, 2010, 7 pp.

\* cited by examiner

A.

B.

C.

D.

E.

F.

SEQUENCE LISTING

<160> NUMBER OF SEQ ID NOS: 3

<210> SEQ ID NO 1
<211> LENGTH: 23
<212> TYPE: DNA
<213> ORGANISM: Artificial
<220> FEATURE:
<223> OTHER INFORMATION: PCR primer

<400> SEQUENCE: 1
tcatagcccc aagtggaggg aga                                    23

<210> SEQ ID NO 2
<211> LENGTH: 24
<212> TYPE: DNA
<213> ORGANISM: Artificial
<220> FEATURE:
<223> OTHER INFORMATION: PCR primer

<400> SEQUENCE: 2
ggttcatatc cccgagctca ggag                                   24

<210> SEQ ID NO 3
<211> LENGTH: 24
<212> TYPE: DNA
<213> ORGANISM: Artificial
<220> FEATURE:
<223> OTHER INFORMATION: PCR primer

<400> SEQUENCE: 3
ggaacttcct gactagggga ggag                                   24

MOUSE MODEL OF CHOLINERGIC DYSFUNCTION TO EVALUATE COGNITIVE ENHANCERS AND DRUGS THAT IMPROVE MYASTHENIA

RELATED APPLICATIONS

This application claims the benefit under 35 U.S.C. §119 (e) of U.S. Provisional Patent Application Ser. No. 60/838,979, filed Aug. 21, 2006, the disclosure of which is incorporated herein by reference in its entirety.

STATEMENT OF GOVERNMENT SUPPORT

This invention was made with Government support under grant no. RO3 TW007025-01A1 from the National Institutes of Health. The United States Government has certain rights to this invention.

FIELD OF THE INVENTION

The present invention concerns transgenic non-human animals and methods of making and using the same.

BACKGROUND OF THE INVENTION

Acetylcholine (ACh) plays a crucial role in controlling a number of physiological processes both in the peripheral and central nervous systems. Synthesis of ACh requires efficient uptake of choline by the high-affinity choline transporter and choline acetylation by the enzyme choline acetyltransferase (CHAT) (Ribeiro et al. (2006) The "ins" and "outs" of the high-affinity choline transporter CHT1. *J. Neurochem.* 97:1-12). Efficient release of ACh from nerve-endings depends on its storage in synaptic vesicles, a step reliant on the activity of a vesicular acetylcholine transporter (VAChT) (Parsons (2000) Transport mechanisms in acetylcholine and monoamine storage. *FASEB J.* 14:2423-2434). VAChT is a twelve-transmembrane domain protein that uses the electrochemical gradient generated by a V-type proton ATPase to accumulate ACh in synaptic vesicles. VAChT and the vesicular monoamine transporters (VMATs) share a high degree of homology in their transmembrane domains and belong to the SLC18 (solute carrier) family of proton/neurotransmitter antiporters (Erickson et al. (1994) Functional identification of a vesicular acetylcholine transporter and its expression from a "cholinergic" gene locus. *J. Biol. Chem.* 269:21929-21932; Reimer et al. (1998) Vesicular neurotransmitter transport and the presynaptic regulation of quantal size. *Curr. Opin. Neurobiol.* 8:405-412; Roghani et al. (1994) Molecular cloning of a putative vesicular transporter for acetylcholine. *Proc. Natl. Acad. Sci. U.S.A.* 91:10620-10624).

The ACh transporter is likely to provide stringent control of the amount of neurotransmitter stored and released by cholinergic nerve-endings (Prado et al. (2002) Regulation of acetylcholine synthesis and storage. *Neurochem. Int.* 41:291-299). VAChT trafficking to secretory vesicles appears to be the target of cellular regulation, and phosphorylation by protein kinase C (PKC) influences delivery of VAChT to synaptic-like microvesicles in PC12 cells (Cho et al. (2000) Phosphorylation of the rat vesicular acetylcholine transporter. *J. Biol. Chem.* 275:19942-19948; Krantz et al. (2000) A phosphorylation site regulates sorting of the vesicular acetylcholine transporter to dense core vesicles. *J. Cell Biol.* 149:379-396). However, the consequences of reduced targeting of VAChT to synaptic vesicles for ACh output in vivo are unknown.

Deficits in central or peripheral ACh neurotransmission have been described in several human disorders, including Alzheimer's disease (AD), in which certain behavioral and cognitive abnormalities have been related to brain cholinergic dysfunction. (Bartus et al., (1982) The cholinergic hypothesis of geriatric memory dysfunction. *Science* 217:408-414; Mesulam (2004) The cholinergic lesion of Alzheimer's disease: pivotal factor or side show? *Learn. Mem.* 11:43-49). However, the relationship between cholinergic decline and specific behavioral deficits is still not completely appreciated. Basal forebrain lesions in rats, with immunotoxins targeting the p75 neurotrophin receptor, indicate that ACh plays an essential role in attention (Sarter et al. (2005) Choline transporters, cholinergic transmission and cognition. *Nat. Rev. Neurosci.* 6:48-56), whereas it seems to participate, but it is not essential, in hippocampal-dependent spatial learning and memory (Parent et al. (2004) *Septohippocampal acetylcholine*: involved in but not necessary for learning and memory? *Learn. Mem.* 11:9-20).

SUMMARY OF THE INVENTION

The present invention provides a recombinant non-human mammal having reduced or absent expression of vesicular acetylcholine transporter protein (VAChT) therein as compared to the corresponding wild-type mammal.

In some embodiments, the mammal expresses between 0, 5, 10, 20 or 30 percent, up to 50, 60, 70 or 80 percent of VAChT, as compared to the corresponding wild-type mammal as determined by western blot analysis.

In some embodiments, the mammal has impaired performance in object and social recognition as compared to the corresponding wild-type mammal.

In some embodiments, the mammal has impaired neuromuscular performance as compared to the corresponding wild-type mammal.

In some embodiments, the mammal has impaired autonomic nervous system function as compared to the corresponding wild-type mammal, for example, the mammal has impaired cardiac performance as compared to the corresponding wild-type mammal (e.g., progressive cardiac heart failure with alterations in cardiac physiology and circulation physiology such as alterations in heart rate, arterial pressure, etc.).

In some embodiments the mammal is a VAChT knockout or knockdown mammal. In one particular embodiment the mammal is a VAChT brain-specific conditional knockout mammal.

In some embodiments the mammal contains a brain-specific, or central nervous system specific, reduction (e.g., reduced by the same percentages as described above, or reduced still further) or absence of VAChT expression.

A further aspect of the invention is a method of screening a compound for cholinergic activity or activity in treating a cholinergic neurotransmission disorder, comprising: administering a test compound to a recombinant non-human mammal as described herein; and then detecting the presence or absence of cholinergic activity, or activity in treating a cholinergic neurotransmission disorder, in said mammal.

A further aspect of the invention is a cell such as a nerve cell (e.g., a central nervous system neuron, autonomic system neuron, etc.) isolated from a mammal of as described herein, along with cell cultures comprising, consisting of or consisting essentially of such cells (that is, produced by culturing such cells). Such cells and cell cultures are useful in vitro for, e.g., screening the activity of candidate compounds for their effect on cholinergic neurotransmission, and for their activity in treating cholinergic neurotransmission disorders.

The present invention is explained in greater detail in the drawings herein and the specification set forth below.

DETAILED DESCRIPTION OF THE PREFERRED EMBODIMENTS

Figure 1:
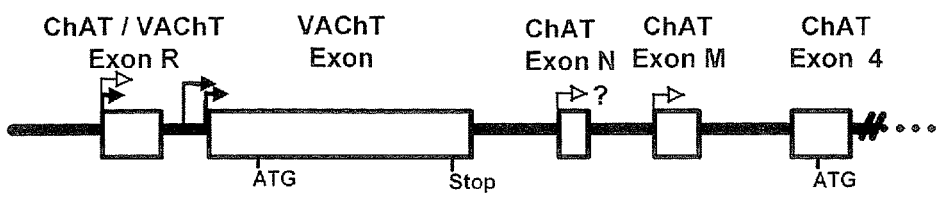
FIG. 1. Schematic drawing of the cholinergic gene locus and generation of VAChT deficient mice. Boxes represent the different exons of ChAT or VAChT. The position of the initiation codon (ATG) for VAChT and ChAT and the stop codon (stop) of VAChT are indicated. Potential transcription initiation sites are indicated for VAChT (filled arrowheads) and ChAT (open arrowheads). Note that the VAChT gene is within the first intron of ChAT. B. Schematic representation of the VAChT gene locus, the targeting construct and the recombinant DNA. P1, P2 and P3 indicate position of PCR primers used for genotyping. ○ indicate loxP sites C. PCR analysis of wild-type (lane 1), heterozygous VAChT KD mice (lane 2) and homozygous VAChT KD mice (lane 3). Lane 4 is a negative control without DNA D. Southern analysis of wild-type (Lanes 1), VAChT KD$^{HET}$ mice (lanes 2) and VAChT KD$^{HOM}$ mice (lane 3). E. Northern blots analysis of VAChT, ChAT and CHT1 in spinal cord for wild-type (lane 1) VAChT KD$^{HET}$ mice (lane 2) and VAChT KD$^{HOM}$ mice (lane 3). Kidney mRNA was isolated and hybridized will all probes similar to nervous tissue and it showed no signal for any of the cholinergic markers. F. Quantification of cholinergic transcripts. Blots were scanned and densitometric analysis was performed using the actin signal to normalize mRNA levels. Data are presented as % of wild-type levels. * indicates statistical significant differences as described in the text.
Figure 1:
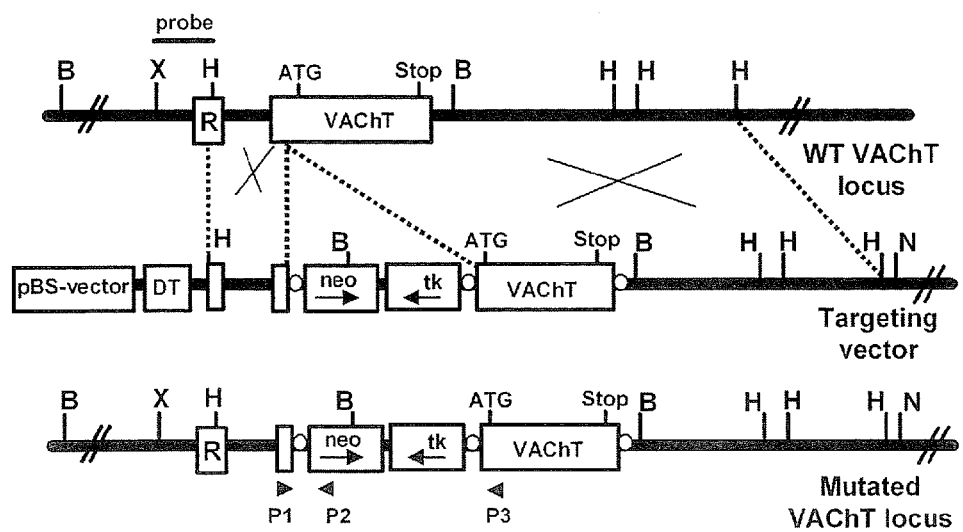
Figure 1:
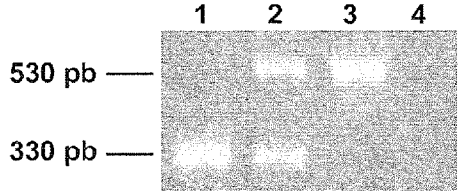
Figure 1:
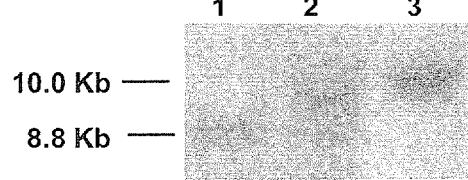
Figure 1:
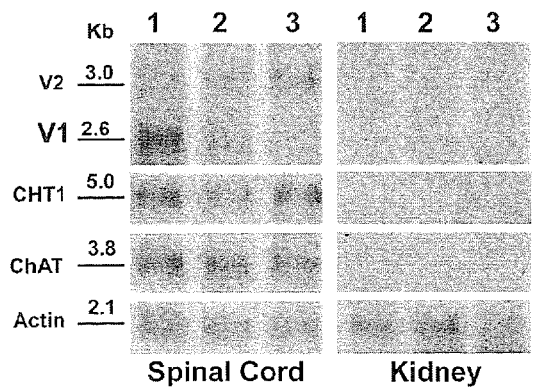
Figure 1:
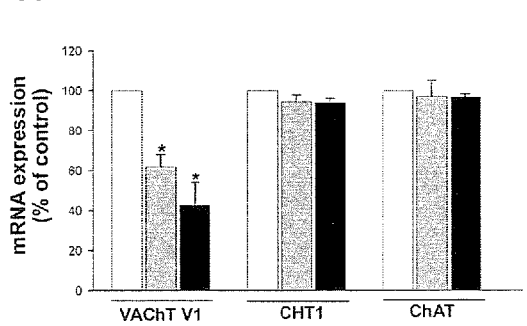
Figure 2:
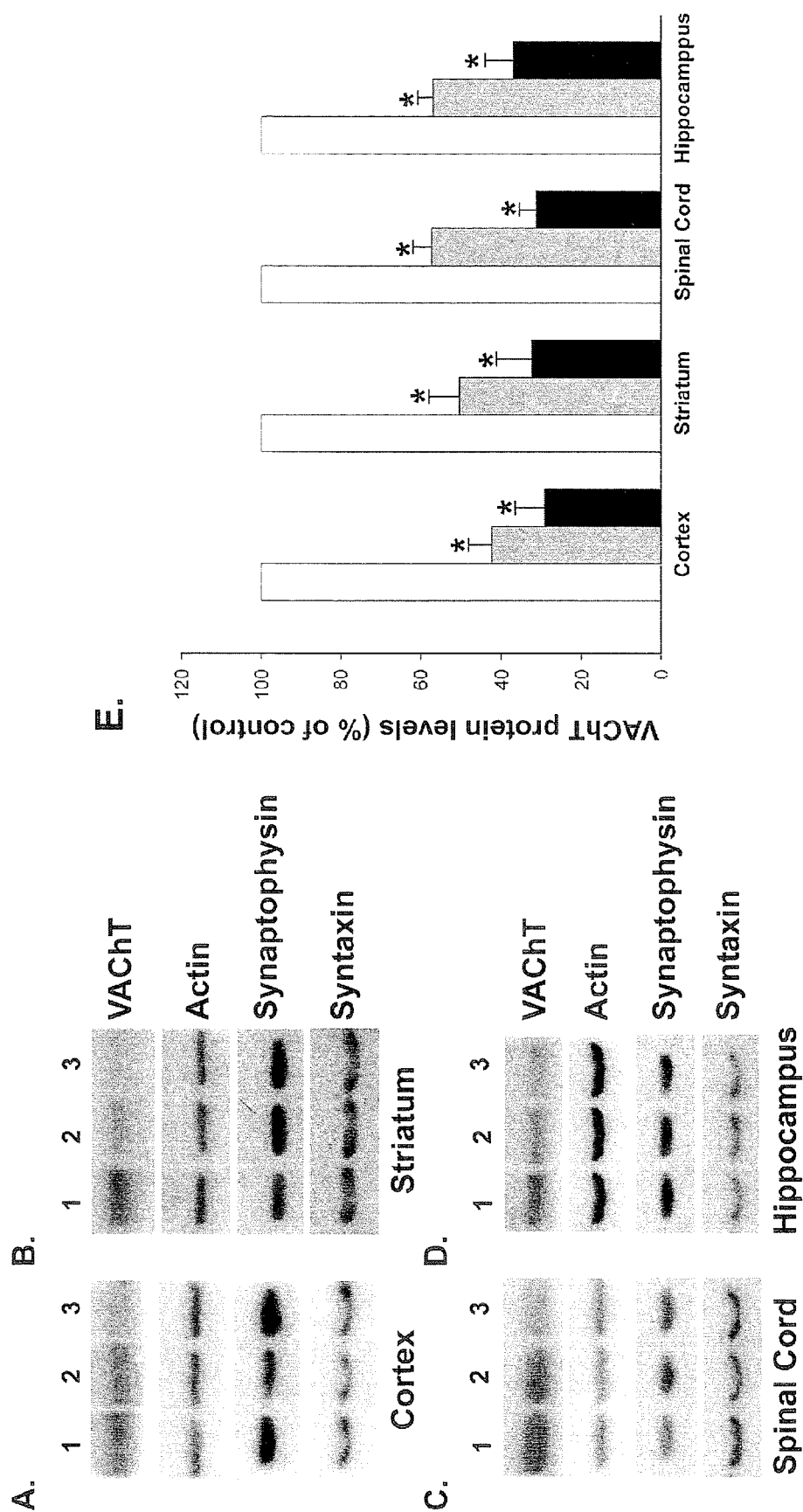
FIG. 2. Gene targeting altered VAChT protein levels. Western blot analysis of VAChT, synaptophysin and syntaxin in the cortex (A.), striatum (B.), spinal cord (C.) and hippocampus (D.) of wild-type (lanes 1), VAChT KD$^{HET}$ (lanes 2) and VAChT KD$^{HOM}$ mice. E. Quantification of protein levels. Actin immunoreactivity was used to correct for protein loading between experiments. Data are presented as % of wild-type levels. * indicates statistical significant difference (One-way Anova with Bonferroni post-hoc (cortex $F_{(2,9)}=49.11$ $p<0.001$; striatum $F_{(2,6)}=27.24$ $p<0.001$; spinal cord $F_{(2,9)}=95.75$ $p<0.001$; Hippocampus $F_{(2,23)}=70.95$ $p<0.001$).

The present invention is explained in greater detail in the non-limiting embodiments described further below. The disclosures of all United States patent references cited herein are to be incorporated by reference herein in their entirety.

"Cholinergic disorder" as used herein includes cholinergic deficit states, examples of which include but are not limited to neurodegenerative diseases such as amyotrophic lateral sclerosis, Alzheimer's disease, Parkinson's Disease, senile dementia, multi-infarct dementia, Huntington's Disease, cerebral palsy, mental retardation, memory loss, neuromuscular diseases such as myasthenia gravis, and disorders of the autonomic nervous system such as familial dysautonomia (see, e.g., U.S. Pat. No. 7,083,930), as well as tardive dyskinesia, and dementia associated with Down's syndrome or Parkinson's disease (see, e.g., U.S. Pat. No. 4,816,456).

Animals of the present invention are, in general, mammals including primates, such as monkeys, more preferably rodents, and are more particularly mice and rats. Animals may be male or female, and may be of any age including adult. In some embodiments animals are laboratory animals (e.g., monkeys, rodents, dogs, pigs, birds, etc.). In some embodiments animals are mammalian laboratory animals (e.g., monkey, rodents, dogs, pigs, etc.). In some embodiments animals are non-human primates, domestic livestock (e.g., horses, cattle, sheep, pigs and goats, and the like), or companion animals (e.g., cats, dogs, guinea pigs, gerbils, hamsters, and the like).

A "recombinant" or "transgenic" non-human mammal refers to a non-human mammal that has a genome or genetic material that is augmented or altered in some fashion with a construct comprising a recombinant nucleic acid (e.g., a "transgene") that is introduced into one or more of the somatic and germ cells of the mammal. The nucleic acid may be, e.g., of the same species (homologous) or of another species (heterologous) with respect to the host mammal.

A "recombinant" nucleic acid refers to a nucleic acid that has been manipulated in vitro. In some embodiments the nucleic acid may include selection marker coding regions, e.g., a thymidine kinase/neomicine selection marker region. In some embodiments these selection marker regions and/or recombinant genes (e.g., a knockin VAChT gene) are removed in subsequent steps according to known techniques. For example, the selection marker may be "floxed," i.e., flanked by loxP sites that are recognized by Cre recombinase, which allows context-specific excision of the nucleic acid segment situated between the loxP sites. In some embodiments, tissue-specific expression of Cre recombinase allows tissue-specific excision of a knockin VAChT gene.

"Congenic" or "recombinant congenic" strains may be created, which are useful to create non-human mammals (e.g., mice) that are nearly identical except for a selected genotype/phenotype (see, e.g., U.S. Pat. No. 7,202,393 to Matsushima). Congenic animals can be generated by mating two genetically distinct inbred strains and then backcrossing the descendants with one of the parental or ancestral strains (the "recipient" strain), e.g., for two generations, followed by inbreeding sister and brother, with or without selecting for particular markers or phenotypes. Using this method, the recipient on average contributes the greater proportion of the genome to each congenic strain. Backcrossing generally increases homozygosity twice as fast as sibling mating. Other methods of creating congenic strains may also be used, and alternative methods may be used, as will be appreciated by those of skill in the art. For example, the number of backcrosses may vary, resulting in different genomic proportions from the recipient. Selection for the genotype/phenotype of interest may also be performed at certain steps as desired.

A "knockout" of a target gene means an alteration in a host cell genome that results in altered expression of the target gene, e.g., by introduction of a mutation into a coding or noncoding region of the target gene, which mutation alters (and particularly reduces) expression of the target gene. Mammals containing a knockout of vesicular acetylcholine transporter protein (VAChT) may be heterozygous or homozygous with respect to the mutation or insertion that causes the knockout. In some embodiments the native gene is left unaltered but a deletion, substitution or insertion mutation (e.g., an insertion of a sequence of suitable length, e.g., 1 or 2 kilobases up to 5 or 6 kilobases, preferably containing one or more selection markers such as neo and/or TK) is introduced into a non-coding region of the gene, such as the 5'untranslated region of the VAChT gene, to interfere with and reduce, but not totally eliminate, VAChT expression. Such a technique is referred to as a "knock-down" (KD) technique herein, and is to be construed as a particular embodiment of a knockout of the said target gene. The term "knockout mouse"

is intended to encompass "conditional knockout mouse," discussed in greater detail below.

"Conditional knockout mouse" as used herein refers to a mouse in which the knockout gene (VAChT herein) is selectively knocked out in a particular tissue (such as brain neurons or central nervous system neurons) and/or at a particular time of development. Such conditional knockout mice can be produced by a variety of techniques, such as with site-specific recombinases such as Cre/lox (to create "floxed" mice or mice having a "flexed" gene) or TnpI/TRT (see, e.g., U.S. Pat. No. 7,083,976), with a tetracycline-controllable transactivator (see, e.g., U.S. Pat. Nos. 6,783,757 and 6,252,136), etc.

"Floxed mice" or "Cre/lox conditional knockout mice" are known. The Cre recombinase catalyzes recombination between 34 bp loxP recognition sequences (Sauer, B. and Henderson, N., Proc. Natl. Acad. Sci. USA 85:5166-5170, 1988). The loxP sequences can be inserted into the genome of embryonic stem cells by homologous recombination such that they flank one or more exons of a gene of interest (making a "floxed" gene). It is crucial that the insertions do not interfere with normal expression of the gene. Mice homozygous for the floxed gene are generated from these embryonic stem cells by conventional techniques and are crossed to a second mouse that harbors a Cre transgene under the control of a tissue type- or cell type-specific transcriptional promoter. In progeny that are homozygous for the floxed gene and that carry the Cre transgene, the floxed gene will be deleted by Cre/loxP recombination, but only in those cell types in which the Cre gene-associated promoter is active. See U.S. Pat. No. 6,583,333; see also U.S. Pat. No. 6,946,244.

An "RNAi knockdown" of a target gene means an alteration in a host cell genome that results in altered expression of the target gene, e.g., by introduction of a expression cassette that encodes an oligonucleotide that binds to the target gene or its transcripts to decrease expression thereof. Mammals containing a knockdown of VAChT may be heterozygous or homozygous with respect to the insert that expresses the sequence responsible fo the RNAi of VAChT mRNA. See, e.g., D. Pawitt et al., RNAi-knock-down mice: an emerging technology for post-genomic functional genetics, *Cytogenet. Genome Res.* 105 (2-4): 412-21 (2004). RNAi knockdown mice are to be distinguished from those knockdown mice that represent a particular embodiment of "knockout" mice as discussed above.

A "knock-in" of a target gene generally refers to the replacement of endogenous genetic material (e.g., a gene or a portion of a gene) with exogenous genetic material (i.e., a recombinant nucleic acid). The term "knock-in" as used herein also includes alterations of genetic material by introduction of one or more additional copies of the recombinant nucleic acid, with or without replacing the endogenous gene. The term "knock-in" is intended to include first generation mice as well as progeny thereof that have the transgene in at least one allele thereof. Non-human mammals may be heterozygous or homozygous with respect to the mutation or insertion that causes the knock-in. For example, in some embodiments an animal in which an additional VAChT gene is heterozygous or homozygous can have reduced expression of VAChT by means of a heterozygous or homozygous knockout of the endogenous VAChT gene.

By the term "express" or "expression" of a nucleic acid coding sequence, it is meant that the sequence is transcribed, and optionally, translated. Transcription can be measured by, e.g., measuring the relative levels of mRNA expression (e.g., with a northern blot, quantitative PCR, etc.), or any means well known by those of skill in the art. Typically, expression of a coding region will result in production of the encoded protein or polypeptide (measured by, e.g., western blot).

The production of transgenic animals, including "knockout," "knockin," and "knockdown" animals, is known and can be carried out in accordance with known techniques or variations thereof which will be apparent to those skilled in the art, for example as disclosed in: U.S. Pat. No. 7,022,893 to to Takeda et al. and U.S. Pat. No. 6,218,595 to Giros et al., as well as U.S. Pat. No. 6,344,596 to W. Velander et al. (American Red Cross); U.S. Pat. No. 6,339,183 to T. T. Sun (New York University); U.S. Pat. No. 6,331,658 to D. Cooper and E. Koren; U.S. Pat. No. 6,255,554 to H. Lubon et al. (American National Red Cross; Virginia Polytechnic Institute); U.S. Pat. No. 6,204,431 to P. Prieto et al. (Abbott Laboratories); U.S. Pat. No. 6,166,288 to L. Diamond et al. (Nextran Inc., Princeton, N.J.); U.S. Pat. No. 5,959,171 to J. M. Hyttinin et al. (Pharming BV); U.S. Pat. No. 5,880,327 to H. Lubon et al. (American Red Cross); U.S. Pat. No. 5,639,457 to G. Brem; U.S. Pat. No. 5,639,940 to I. Garner et al. (Pharmaceutical Proteins Ltd.; Zymogenetics Inc); U.S. Pat. No. 5,589,604 to W. Drohan et al. (American Red Cross); U.S. Pat. No. 5,602,306 to Townes et al. (UAB Research Foundation); U.S. Pat. No. 4,736,866 to Leder and Stewart (Harvard); and U.S. Pat. No. 4,873,316 to Meade and Lonberg (Biogen).

Progeny of first generation animals produced by the methods described herein are also an aspect of the present invention. Such animals, or congenic animals, of the invention can be produced in accordance with known techniques, including but not limited to those described in U.S. Pat. No. 6,465,714, the disclosure of which is incorporated by reference herein in its entirety. In general, animals of the present invention are created by (a) providing a first (male or female) recombinant parent animal produced as described above, and a second parent animal, wherein at least the first parent exhibits the phenotype of the invention (e.g., decreased brain VAChT levels); and then (b) crossing the first and second parent mice with one another to produce a progeny mouse that exhibits that phenotype. Subsequent generations can be further produced in accordance with known techniques.

"Wild type" gene sequences of a given species are those DNA or protein sequences that are most highly conserved within or across species and/or which are generally accepted as the wild type gene in the art. For example: Genbank accession number: NM_003055, accession number human sequence; NM_021712 accession number mouse sequence (see also Alfonso et al. (1993) The *Caenorhabditis elegans* unc-17 gene: a putative vesicular acetylcholine transporter. *Science* 261:617-619; Erickson et al. (1994) Functional identification of a vesicular acetylcholine transporter and its expression from a "cholinergic" gene locus. J Biol Chem. 269:21929-32; Roghani et al. (1994) Molecular cloning of a putative vesicular transporter for acetylcholine. *Proc Natl Acad Sci USA* 91:10620-4; Barbosa et al. (1999) Expression of the vesicular acetylcholine transporter, proteins involved in exocytosis, and functional calcium signaling in varicosities and soma of a murine septal cell line. *J Neurochem* 73:1881-93; Ferreira et al. (2005) Structural requirements for steady-state localization of the vesicular acetylcholine transporter. *J Neurochem* 94:957-69).

Accordingly, in some embodiments a "wild type" non-human mammal is one that does not contain a mutant VAChT gene or a mutant VAChT transgene, including, but not limited to, alterations (e.g., additions) of recombinant nucleic acids to coding and/or non-coding regions of the VAChT gene (e.g., the 5' untranslated region). In preferred embodiments, the genome or genetic material of the wild type mammal is otherwise significantly or substantially identical to the transgenic, recombinant and/or congenic non-human mammal having a mutant VAChT gene (e.g., littermates). Non-human animals of the present invention are, in general, mammals, including primates, such as monkeys, more preferably rodents, and are more particularly mice and rats. Animals may be male or female, and may be of any age including adult.

In some embodiments, the mammal has impaired performance in "object and social recognition," as measured by, e.g., a step-down inhibitory avoidance task, an object recognition task, a habituation-dishabituation paradigm, an evaluation of sociability, an evaluate the olfactory response, etc.

In some embodiments, the mammal has impaired "neuromuscular performance." In some embodiments, this may be measured by, e.g., Miniature End-Plate Potentials (MEPPs) (e.g., quantal size, frequency, etc.) at a neuromuscular junction. In other embodiments, this may be measured by, e.g. a wire-hang, grip force, rotarod and/or treadmill tests, etc.

In some embodiments, the mammal has impaired "cardiac performance," as measured by, e.g., progressive cardiac heart failure with alterations in cardiac physiology and circulation physiology such as alterations in heart rate, arterial pressure, etc.

As noted above, the present invention provides methods of screening a compound for cholinergic activity or activity in treating a cholinergic neurotransmission disorder. In some embodiments the method comprises administering a test compound to a mammal as described herein, and then detecting the presence or absence of cholinergic activity in a biochemical or behavioral assay, or activity in treating a cholinergic neurotransmission disorder, in the mammal. The administering step may be carried out by any suitable technique depending upon the particular compound, including parenteral injection, oral administration, inhalation administration, transdermal administration, etc. The detecting step may also be carried out by any suitable technique for measuring motor or cognitive performance in the mammal, or for measuring cholinergic neurotransmission in the mammal, such as by a wire-hang, grip force, rotarod, treadmill, step-down inhibitory avoidance, object recognition, or social recognition test.

The present invention is explained in greater detail in the following non-limiting Examples.

Example 1

To investigate the consequences of reduced expression of VAChT on ACh neurotransmission and function, we genetically modified mice to produce a knock-down (KD) of VAChT gene expression. The partial decrease in VAChT expression is essential in these investigations as complete lack of the vesicular transporter is likely to be incompatible with life, as shown for other pre-synaptic cholinergic genes (Brandon et al. (2004) Choline transporter 1 maintains cholinergic function in choline acetyltransferase haploinsufficiency. *J. Neurosci.* 24:5459-5466; Ferguson et al. (2004) Lethal impairment of cholinergic neurotransmission in hemicholinium-3-sensitive choline transporter knockout mice. *Proc. Natl. Acad. Sci. U.S.A.* 101:8762-8767; Misgeld et al. (2002) Roles of neurotransmitter in synapse formation: development of neuromuscular junctions lacking choline acetyltransferase. *Neuron* 36:635-648). Thus, this mouse lines allowed us to examine the consequences of reduced cholinergic tone in cholinergic neurochemistry, function and behavior.

We observed a strong relationship between the levels of VAChT expression and ACh release both in the peripheral and central nervous systems. A marked reduction of VAChT expression was necessary to affect neurotransmission at the neuromuscular junction, whilst even modest deficiency was sufficient to interfere with brain ACh release and affect behavior. Moreover, these investigations revealed a role for cholinergic tone in processing complex cues, which reflected in cognitive deficits in mutant mice for object and social memory.

PCR and Southern analyses confirmed homologous recombination and targeting of the 5'untranslated region of the VAChT gene in genetically altered mice (FIG. 1C and FIG. 1D). Mutant mice were born at the expected Mendelian frequency, survived and exhibited no gross abnormalities. Heterozygous ($KD^{HET}$) mice were backcrossed with C57BL/6J animals for 3 generations; the N3 mice were used in most experiments. Homozygous mutant VAChT mice ($KD^{HOM}$) were obtained by intercrossing N3 heterozygous animals. Control animals were wild-type age and sex matched littermates and all behavioral and most of the biochemical studies were conducted with researchers "blind" to the genotypes of the mice. For all behavioral experiments male mice were used.

Animals were housed in groups of 3-5 animals/cage in a temperature-controlled room with a 12:12 light-dark cycles and food and water were provided ad libitum. All studies were conducted in accordance with NIH guidelines for the care and use of animals and with approved animal protocols from the Institutional Animal Care and Use Committees at the Federal University of Minas Gerais, Pontificia Universidade Catolica de Rio Grande do Sul in Brazil, and at Duke University in the United States.

Genetic Targeting of the VAChT Gene Locus.

In order to decrease the expression of VAChT, we targeted the "cholinergic gene locus" by homologous recombination, as shown in FIG. 1A. The rationale for this approach was to introduce the selection marker cassette within the 5'untranslated region of the VAChT gene to interfere with VAChT expression, without suppressing it, to allow survival of mice for behavioral studies. Using a VAChT cDNA probe, we screened a mouse 129/SvJ genomic library and isolated a phage clone of approximately 19 kb that contained the complete ORF for VAChT, as well as upstream and downstream sequences. This genomic clone was used to construct a gene-targeting vector containing 9 kb of homologous DNA downstream of the TK-Neo cassette and 1.4 kb of homologous DNA upstream from the cassette (FIG. 1B). The linearized targeting vector was electroporated into J1 ES cells derived from 129/terSv mice and selected ES cell clones harboring homologous recombination (determined by PCR and Southern blot, not shown) were injected into C57BL/6 blastocysts to produce chimeric mice. Germline transmission was achieved and mice were bred to C57BL/6 mice to produce heterozygote mutant mice. This manipulation generated mice with knock-down (KD) of VAChT expression, and we denote $KD^{HET}$ for heterozygous and $KD^{HOM}$ for homozygous mice.

PCR, Southern, Northern and Quantitative PCR Analysis.

Genotyping by PCR was performed using tail DNA as template. The 3 primers used were: a common wild-type and Knock-down (KD) sense oligonucleotide primer: (VATS, 5' TCATAGCCCCAAGTGGAGGGAGA 3' SEQ ID: 1), a wild-type antisense primer (336 bp from VATS primer in wild-type allele, VATAS 5'-GGTTCATATCCCCGAGCT-CAGGAG 3' SEQ ID: 2), and a KD reverse primer (528 bp from VATS primer in the KD allele, 5'-GGAACTTCCTGAC-TAGGGGAGGAG-3' SEQ ID: 3).

For Southern analysis genomic DNA was digested with BamHI, run in 0.7% agarose gel and transferred to a nylon membrane. After crosslinking, the membrane was blocked with hybridization solution (6×SSC, 5×Denhardt's solution, 0.5% SDS, 50% formamide and 100 µg/ml of salmon sperm DNA) and hybridized at 60° C. to $^{32}$P-labeled 650 bp XhoI-HindIII VAChT DNA fragment overnight (FIG. 1). The membrane was washed at 60° C. in 0.2×SSC, 0.1% SDS followed by autoradiography for 48 h at −70° C. with an enhancing screen.

For RNA purifications, tissues were grounded in a potter and pestle with liquid nitrogen and total RNA was extracted using Trizol (Invitrogen, São Paulo, Brazil). mRNA purification was done using the Poly(A) Purist™ mRNA Purification Kit from Ambion (Tex. USA) according to manufacturer instructions. Ten µgs of mRNA pooled from 8 animals were resolved in 1% agarose gel and transferred to a nylon membrane. Northern blots were prepared using the Northern-Max® Kit from Ambion. $^{32}$P-labeled probes based on the VAChT, high-affinity choline transporter (CHT1) and choline acetyltransferase (ChAT) gene were used (sequence available upon request). The levels of mRNA in the gel were normalized using a probe for β-actin supplied with the kit and quantified by densitometry. Because of the large number of animals needed to detect VAChT transcripts, we pooled the data obtained from northern blots of the spinal cord and brain stem for quantification. The membranes were incubated with the respective probes for several hours at 42° C. and washed according to instructions of the manufacturer.

For quantitative PCR (qPCR), total RNA was treated with DNase I (Ambion, Austin, Tex. USA) and first strand cDNA was synthesized using oligo dT from Superscript™ First-Strand Synthesis for RT-PCR (Invitrogen, São Paulo, Brazil) according to manufacturer's instructions. After reverse transcription, the cDNA was diluted and subjected to qPCR on a SmartCycler™ thermocycler (Cepheid, Calif. USA) using Platinum SYBR Green qPCR SuperMix-UDG (Invitrogen). Briefly, amplification was carried out in a total volume of 25 µl containing 0.4 mM of each primer, 8 µl of SYBR Green Supermix 2× and 2 µl of 1:10 diluted cDNA. The PCR reactions were cycled 45 times after initial denaturation (95° C., 2 minutes) with the following parameters: 95° C., 15 s; annealing 60° C., 30 s, extension 72° C., 30 s. For each experiment, a non-template reaction was included as negative control. In addition, the absence of DNA contaminates was assessed in RT-negative samples. Melting curve analysis of amplification products was performed by cooling the samples to 60° C. and then increasing the temperature to 95° C. at 0.1° C./s. The specificity of the PCR reactions was also confirmed by size verification of the amplicons in acrylamide gel. Relative quantification of gene expression was done with the $2^{-\Delta\Delta Ct}$ method using the beta actin gene expression to normalize the data.

Western Blot Analysis.

Tissues were frozen in a mixture of dry ice/ethanol and kept at −80° C. until use. For preparation of extracts, tissues were homogenized in a solution containing 10 mM Tris-HCl pH 7.5, 150 mM NaCl, 1 mM EDTA, 1% Triton X-100 and protease inhibitor cocktail (Sigma Chem. Co., São Paulo, Brazil). Extracts remained on ice for 15 min and were then centrifuged (10,000×g×20 min) at 4° C. Protein concentration in the supernatant was determined using the method of Bradford (Bradford, 1976). Samples were resolved in precast gels (Invitrogen, 4-12%) and transferred to nitrocellulose membranes. Immunoblotting was performed as described elsewhere (Ribeiro et al., 2005). Antibodies used were: anti-VAChT (Phoenix Pharmaceuticals, Belmont Calif.), antisynaptophysin (Sigma Chemical Co., SP, Brazil), anti-Synaptotagmin (Synaptic Systems Gottingen, Germany) and anti-actin (Chemicon, Calif. USA). Blots were developed using the Enhanced Chemiluminescence Kit (GE Healthcare, São Paulo, Brazil) according to the supplier's instructions. Non-saturated autoradiographs were digitalized and analyzed with Image J software, available on-line from the NIH.

Choline Acetyltransferase Activity.

ChAT activity was determined in accordance with known techniques. Briefly, tissue was homogenized (10% p/v) in 40 mM phosphate buffer (pH 7.4), 200 mM NaCl, 0.5% Triton X-100. Tissue extract was incubated with buffer containing 0.25 mM [acetyl-1-$C_{14}$] acetyl-CoA (GE Healthcare, SP, Brazil) for 10 min at 37° C. Reaction was stopped and radiolabeled ACh recovered by extraction in tetraphenyborum in butyronitrile. Radioactivity was measured with a Liquid Scintillation Counter (Packard—PerkinElmer Life Science, Boston, Mass. USA) in accordance with known techniques.

Figure 6:
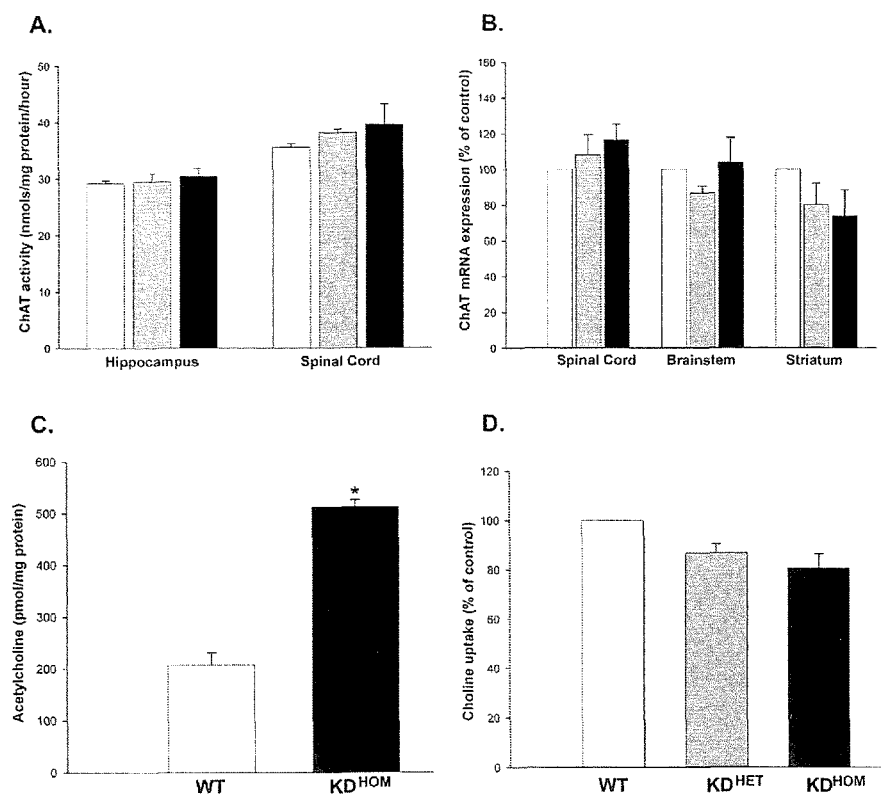
FIG. 6. VAChT KD$^{HOM}$ mice show an even larger increase in ACh content in the brain and this was statistically different from VAChT KD$^{HET}$ mice or wild-type mice (C; $p<0.05$). This increase in ACh content for mutant mice cannot be attributed to an increase in CHAT activity (A), high-affinity choline transporter activation (D), or increased levels of expression of ChAT (B) or CHT1.

Northern analysis of spinal cord indicated that the major mRNA species for VAChT (V1, 2.6 kb) was significantly reduced by 40 and 62% in VAChT $KD^{HET}$ and $KD^{HOM}$ mice respectively ($F(2,11)=11.09$ $p<0.005$, One-way ANOVA, FIG. 1E and FIG. 1F). Surprisingly, a second VAChT species of 3.0 Kb, that was especially apparent in spinal cord, was significantly increased in VAChT KD mice, suggesting that compensatory transcriptional mechanisms operate in response to changes in VAChT expression. The changes in mRNA were specific for VAChT transcripts, as we detected no significant changes in mRNA levels for ChAT ($F(2,3)=0.0311$ $p=0.970$) and CHT1 ($F(2,12)=0.0921$ $p=0.9127$) in mutant mice (FIG. 1E and FIG. 1F). These results agree with the lack of significant alterations found in ChAT activity and high affinity choline transport in mutant mice (see FIG. 6). Control experiments using kidney mRNA demonstrated the specificity of the probes (FIG. 1E).

We investigated the consequences of altered expression of VAChT mRNA in VAChT KD mice by probing protein expression by immunoblot analysis. These experiments show a reduction of close to 50% in immunoreactivity for VAChT in the hippocampus (Two-way ANOVA followed by Bonferroni post-hoc, $F(2,23)=70.95$ $p<0.001$, FIG. 2D and FIG. 2E) and in other brain regions (FIG. 2A-E) of VAChT $KD^{HET}$ mice compared to wild-type control mice. In contrast, levels of other presynaptic proteins were not altered (FIG. 2A-E). Results were similar in all brain regions and in the spinal cord (FIG. 2E, overall decrease in all tissues 56±4% of the wild-type levels, N=20). These results indicate a significant reduction in VAChT protein in VAChT $KD^{HET}$ mice. VAChT $KD^{HOM}$ mice showed further decrease in VAChT protein levels (65 to 70%, FIG. 2A-E). Thus, VAChT $KD^{HOM}$ mice present an even larger decrease in levels of transporter than VAChT $KD^{HET}$ mice, but VAChT expression in homozygous mutant mice is sufficient for survival.

Electrophysiological Analysis and Neuromuscular Function.

Figure 3:
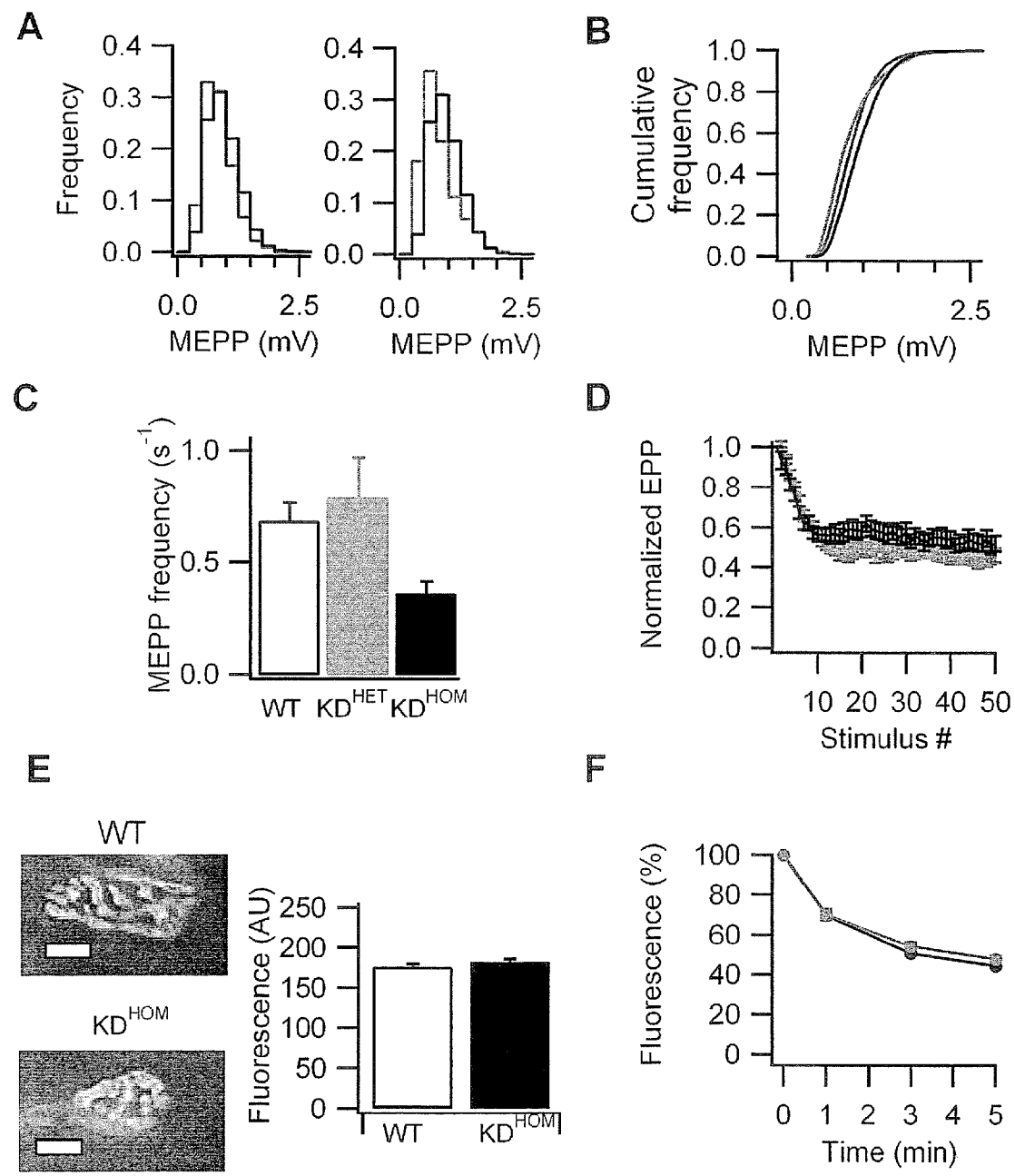
FIG. 3. Neuromuscular transmission in VAChT KD$^{HET}$ and VAChT KD$^{HOM}$ mice. A. Normalized histogram of MEPP amplitudes for wild-type (black line, 3302 MEPPs), VAChT KD$^{HET}$ (blue line, 4319 MEPPs) and VAChT KD$^{HOM}$ (red line, 3690 MEPPs) mice. Data are from 5 synapses from 5-7 animals for each genotype B. Quantal size of the three genotypes quantified by plotting the cumulative frequency of MEPP amplitudes. Black line: WT. Blue line: VAChT KD$^{HET}$ Red line: VAChT KD$^{HOM}$. C. Frequency of MEPPs at synapses from the three genotypes. * indicates statistically significant difference from control wild-type mice (Two-way ANOVA followed by Bonferroni post-hoc, $(F_{(1,18)}=10.3,$ $p<0.005$). D. Normalized EPP amplitude (to the first stimulus) for wild-type (black line) and VAChT KD$^{HOM}$ mice (red line) in response to a train of 100 Hz (0.5 sec) Data are from 10 synapses from 3 wild-type animals and 16 synapses from 3 KD$^{HOM}$ animals E. Nerve terminals from wild-type and VAChT KD$^{HOM}$ mice were labeled with FM1-43 and show similar patterns of staining. Data are mean±SEM of 109 fluorescent spots from 21 nerve terminals of wild-type mice and 111 fluorescent spots from 26 nerve terminals from VAChT KD$^{HOM}$ F. Destaining of FM1-43 labeled nerve endings from wild-type (black line) and VAChT KD$^{HOM}$ (red line). Data are mean±SEM of 26 fluorescent spots (wild-type mice) and 21 fluorescent spots (VAChT KD$^{HOM}$) from 4 mice/genotype.

In order to evaluate the consequences of reduced VAChT expression for quantal ACh release we examined neuromuscular transmission. Miniature End-Plate Potentials (MEPPs) were readily recorded at neuromuscular junctions from either wild-type, VAChT $KD^{HET}$ or VAChT $KD^{HOM}$ mice. To compare quantal size we recorded at least 100 MEPPs from each of five fibers from 5-7 animals of each genotype. MEPPs from mutant mice were smaller than wild-type, as can be seen in histograms of MEPP amplitudes (FIG. 3A). To avoid possible histogram binning artifacts, we also analyzed the cumulative distribution of MEPP amplitudes, which showed a similar shift to smaller MEPPs in mutant animals (FIG. 3B, $p<0.001$ by Kolmogorov-Smirnoff test VAChT $KD^{HOM}$ and $p<0.05$ for VAChT $KD^{HET}$). Further statistical analysis using ANOVA on fiber averages of either the peak amplitude or the area of MEPPs confirmed the statistical significance of the differences in quantal sizes between wild-type and VAChT $KD^{HOM}$ animals ($F(1,71)=8.7$, $p<0.005$). Therefore, mutant mice appear to pack less ACh in each synaptic vesicle.

In addition to exhibiting smaller quantal size, MEPP frequency was also strongly reduced in VAChT $KD^{HOM}$ animals, as shown in FIG. 3C. The frequency of MEPPs was $0.69\pm0.08$ $s^{-1}$ in wild-type animals (40 synapses from 7 animals), $0.79\pm0.18$ $s^{-1}$ in VAChT $KD^{HET}$ animals (30 synapses from 5 animals) and $0.37\pm0.05$ $s^{-1}$ in VAChT $KD^{HOM}$ mice (41 synapses from 7 animals). The difference in MEPP frequency between wild-type and VAChT $KD^{HOM}$ mice was statistically significant (Two-way ANOVA followed by Bonferroni post-hoc, $F(1,18)=10.3$, $p<0.005$).

The observed decrease in MEPP frequency at junctions from $KD^{HOM}$ mice could be due to a reduction in the number of synaptic vesicles available for release, a reduction in vesicle release probability, or to a population of synaptic vesicles whose ACh load is below our detection limit. To investigate these possibilities, we measured evoked End-Plate Potentials (EPPs) during 100 Hz trains after cutting the muscle fibers to avoid contraction. Under these conditions, EPP amplitudes during a train rapidly fell from their initial level to a depressed steady-state over the course of the first 10 stimuli (FIG. 3D). Overall, initial depression of normalized EPPs was similar in recordings from wild-type and $KD^{HOM}$ animals, suggesting similar release probabilities. Quantal content of each EPP during a train was calculated based on measured MEPP amplitudes, thus permitting an estimate of the size of the readily releasable pool of vesicles as described (Elmqvist et al. (1965) Presynaptic action of hemicholinium at the neuromuscular junction. *J. Physiol.* 177:463-482). This analysis considered only the first eight responses during a train for which the relationship between EPP versus cumulative EPP was linear. With this method, the readily-releasable pool was similar for both genotypes and estimated at $439\pm73$ vesicles in synapses from wild-type animals and $550\pm59$ vesicles in VAChT $KD^{HOM}$ synapses ($p=0.52$, Two-tailed Student's t test). In contrast, the extent of steady-state depression of EPPs was significantly greater in VAChT $KD^{HOM}$ animals compared to wild-type (One-way ANOVA, $F(1,70)=197$, $p<0.001$).

Assuming constant quantal size, the increase in depression uncovered in the above experiments would suggest a defect in mobilizing or recycling of ACh-filled vesicles, however the assumption of constant quantal size during the stimulus train may not be valid for mutant animals. Therefore, we attempted to directly test whether synaptic vesicle exo- and endocytosis would be altered in mutant mice. For this we performed experiments with the vital dye FM1-43 (Richards et al. (2000) Two endocytic recycling routes selectively fill two vesicle pools in frog motor nerve terminals. *Neuron* 27:551-559) that provides the opportunity for optical detection of both exocytosis and endocytosis of synaptic vesicles.

Labeling of nerve terminals in response to 60 mM KCl (10 min) was indistinguishable in junctions from wild-type and $KD^{HOM}$ animals, and no differences were detected upon quantification of fluorescent spots (FIG. 3E), suggesting that endocytosis occurs to the same extent in both genotypes. Destaining of fluorescent spots in response to 60 mM KCl was calcium dependent (not shown), and was not different between wild-type and $KD^{HOM}$ animals (FIG. 3F), indicating that synaptic vesicle exocytosis is not changed in VAChT $KD^{HOM}$ mice. Thus, taken together, our observations would suggest that the alteration in MEPP frequency and EPP depression in VAChT $KD^{HOM}$ are more than likely a consequence of decreased transport of ACh by synaptic vesicles.

Wire-Hang, Grip Force, Rotarod and Treadmill Tests.

Figure 4:
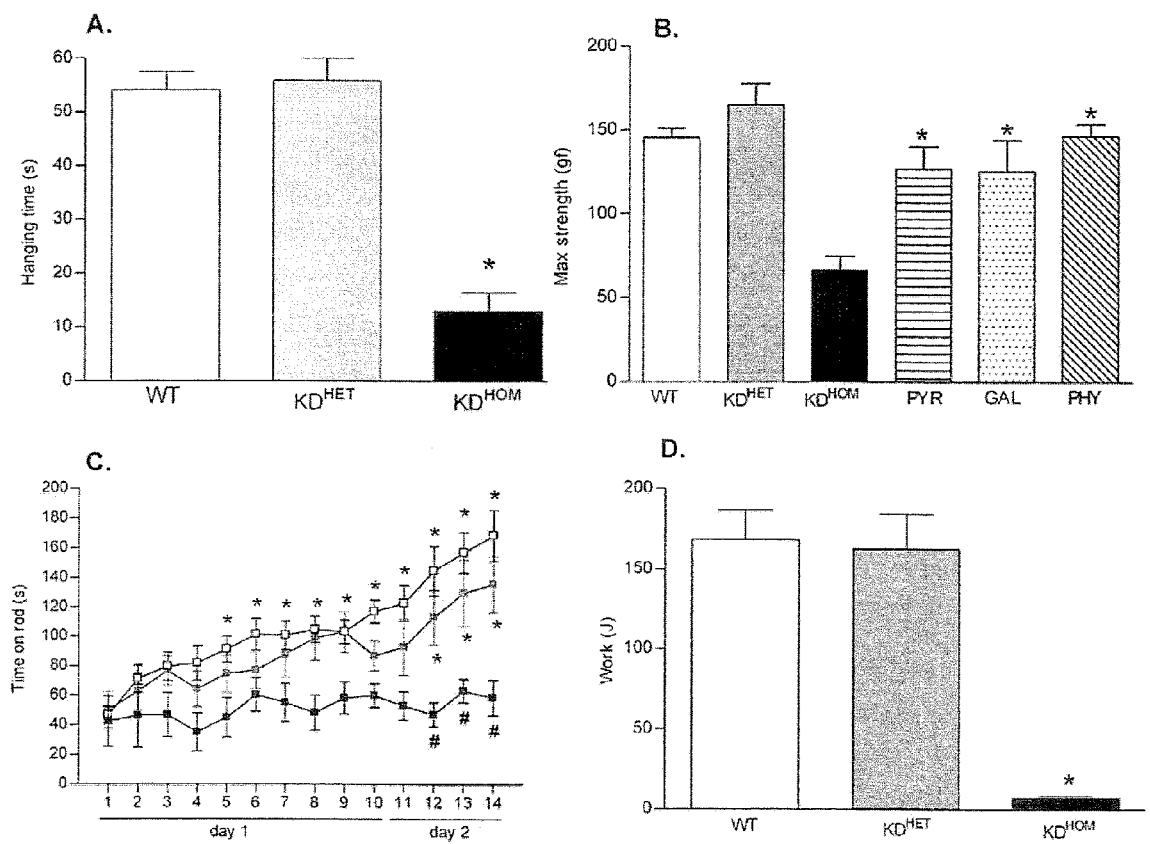
FIG. 4. Neuromuscular function of VAChT KD$^{HET}$ and VAChT KD$^{HOM}$ mice. A. Time spent hanging upside-down from a cage by WT and VAChT KD$^{HET}$ and KD$^{HOM}$ mice. *$p<0.05$ from WT controls (One way ANOVA followed by Bonferroni post-hoc $F_{(2,37)}=28.77$, $p<0.05$, N=20 wild-type, 12 VAChT KD$^{HET}$ and 8 VAChT KD$^{HOM}$). B. Grip-force measured for wild-type, VAChT KD$^{HET}$, VAChT KD$^{HOM}$ mice and VAChT KD$^{HOM}$ treated with pyridostigmine (1 mg/kg i.p.), galantamine (1 mg/kg s.c.) and physostigmine (0.3 mg/kg i.p.) 30 min prior to the test. *indicates statistical difference when compared to VAChT KD$^{HOM}$ mice without cholinesterase treatment C. Performance of wild-type (clear squares), VAChT KD$^{HET}$ (gray squares) and VAChT KD$^{HOM}$ mice (black squares) on the rotarod task. * indicates statistically differences compared to the first trial for each genotype (Repeated Measures ANOVA, $p<0.05$). # indicates statistically different performance when compared to wild-type mice (Two-way ANOVA shows an effect of genotype $F_{(2,434)}=60.16$, $p<0.05$). D. Exercise capacity of wild-type, VAChT KD$^{HET}$ and VAChT KD$^{HOM}$ mice. Mice were trained in the treadmill with a protocol that evaluated physical capacity (see Methods). After training mice were tested for performance and the work (in J) done was calculated.

To evaluate whether the alterations detected in neuromuscular transmission may affect neuromuscular function, we tested the performance of wild-type and mutant mice in motor tasks (FIG. 4). The wire-hang experiments were conducted as described (Sango et al. (1996) Mice lacking both subunits of lysosomal beta-hexosaminidase display gangliosidosis and mucopolysaccharidosis. *Nat. Genet.* 14:348-352) and time spent hanging upside down was determined with a cut-off time of 60 sec. In the wire-hang test (FIG. 4A), wild-type and VAChT $KD^{HET}$ mice show no differences in performance; however VAChT $KD^{HOM}$ mice were significantly impaired ($F(2, 37)=28.77$ $p<0.001$) This altered performance of VAChT $KD^{HOM}$ animals is likely the result of altered neuromuscular force, since these mutants were also severely impaired in a grip-strength test when compared to wild-type mice (FIG. 4B, $F(3,48)=9.52$ $p<0.001$).

To measure grip force, we used a custom built force transducer connected to a small support that could be grasped by the mouse as described (Fowler et al. (2002) Motor and associative deficits in D2 dopamine receptor knockout mice. *Int. J. Dev. Neurosci.* 20:309-321). Five tests were performed per mouse with a maximum period of 50 sec for each animal over two different days. The force transducer was coupled to a computer and a routine was developed to record the maximal grip-force exerted. By comparison, VAChT $KD^{HET}$ mice present no deficit in neuromuscular function as assessed in this test. Importantly, reduced grip-strength in VAChT $KD^{HOM}$ mice was improved by prior injection of one of three cholinesterase inhibitors: pyridostigmine (i.p. 1 mg/kg), galantamine (s.c. 1 mg/kg) or physostigmine (i.p., 0.3 mg/kg), (FIG. 4B, $F(3,47)=8.323$ $p<0.05$). No change in grip-force was observed in wild-type mice treated similarly with any of the above cholinesterase inhibitors at the doses used (not shown). Since pyridostigmine is charged, and should not cross the blood-brain barrier, its efficacy in improving grip-force observed in homozygous mutant mice directly implicates peripheral cholinergic transmission in this effect.

To further study neuromuscular output, we examined performance of VAChT mice on the rotarod. This test depends not only on the ability of mice to learn motor skills, but also to maintain prolonged motor function. For the rotarod task, we followed the protocol described by (Brandon et al. (1998) Defective motor behavior and neural gene expression in RII-beta-protein kinase A mutant mice. *J. Neurosci.* 18:3639-3649). Mice were placed on the rotarod apparatus (Insight Equipments. Ribeirão Preto, Brazil) and rotation was increased from 5 to 35 rpm. Latency to fall was recorded automatically. The test was run within the last 4 hr of the light phase of the 12 h/dark cycle. Ten trials were given on the first day and four trials on the second day with 10 min inter-trial interval. In the time between trials mice were placed in their home cage.

Wild-type mice were able to learn this motor task and after 5 trials their performance was significantly better than at the first trial (FIG. 4C, Repeated Measures ANOVA $F(13,195)=16.9$, $p<0.05$). The performance of VAChT $KD^{HET}$ mice improved only after 12 trials on the rotarod (Repeated Measures ANOVA, $F(13,117)=4.63$ $p<0.05$). In contrast, VAChT $KD^{HOM}$ mice never learned this motor task (FIG. 4C, $F(13,91)=0.653$) and their performance was significantly worse than those of wild-type and VAChT $KD^{HET}$ mice ($F(2,434)=60.16$, $p<0.05$ on trials 12, 13 and 14, two-way ANOVA followed by Bonferroni post hoc tests).

The performance of VAChT $KD^{HOM}$ mice may indicate either motor learning deficits on the rotarod or that mutant mice are incapable of sustained physical activity. To evaluate the latter possibility, we used a treadmill to evaluate the performance of wild-type, VAChT KD$^{HET}$ and VAChT KD$^{HOM}$ mice in exhaustive physical activity. For the treadmill test (Insight Equipments. Ribeirão Preto, Brazil), mice were trained for 4 days (3 min a day). On the first day, inclination was set to 5° and then the inclination was increased by 5° for each training day until reaching 20°. The initial training speed was 8 meters/min and the treadmill was accelerated by 1 meter/min. In the second training session, the initial speed was 10 meters/min and it was increased to 11 and 12 meters/min in the third and fourth training days respectively. During testing, the initial speed was set to 12 meters/min, which was increased by 1 meter/min at times 2, 5, 10, 20, 30, 40, 50 and 60 min after starting the exercise, essentially as described by (Pederson et al. (2005) Exercise capacity of mice genetically lacking muscle glycogen synthase: in mice, muscle glycogen is not essential for exercise. *J. Biol. Chem.* 280:17260-17265). The work performed in (J) was calculated with the following formula W(J)=body weight (Kg)×cos 20°×9.8 (J/kg×m)×distance (m)

FIG. 4D shows that VAChT KD$^{HOM}$ mice were not able to maintain long periods of physical activity and performed poorly compared to wild-type or VAChT KD$^{HET}$ mice (One-way ANOVA followed by Bonferroni post-hoc, $F(2,28)=22.09$, $p<0.001$). Indeed, VAChT KD$^{HOM}$ mice could run no more than 5 minutes on the treadmill, whereas wild-type or VAChT KD$^{HET}$ mice could usually run over 60 minutes. These results indicate that VAChT KD$^{HOM}$ mice are unable to perform on the rotarod due to their decreased capacity to maintain physical activity. They also indicate that VAChT KD$^{HET}$ mice appear as physically fit as wild-type control mice in the conditions tested.

Neurochemical Analysis.

VAChT KD$^{HOM}$ mice display significant neuromuscular deficiency which may confound the outcome of complex behavioral tests aimed in assessing consequences of central ACh deficiency. In contrast, VAChT KD$^{HET}$ mice have essentially normal neuromuscular transmission thereby providing test subjects to investigate the behavioral consequences of mild reductions of central cholinergic function.

Figure 5:
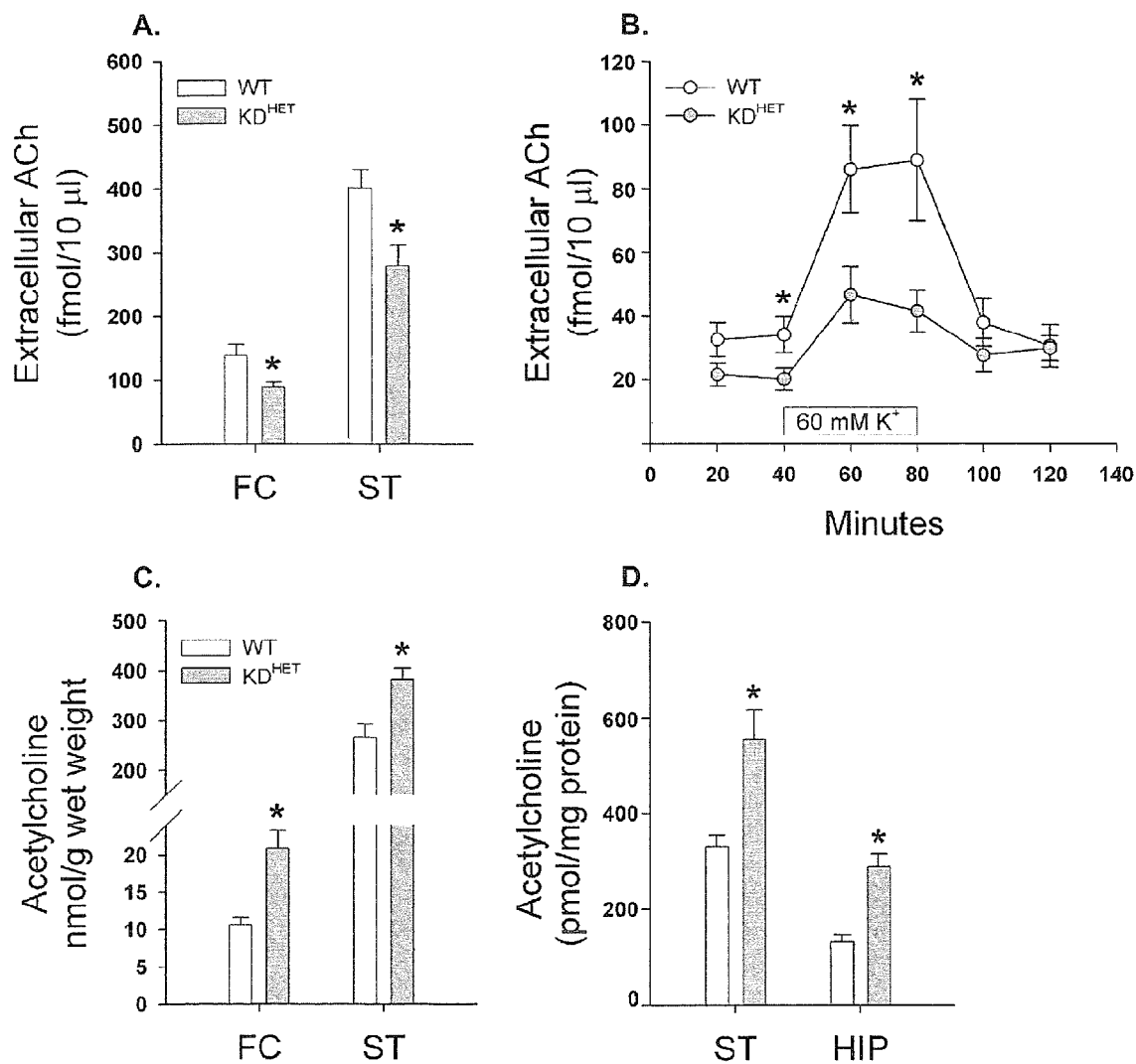
FIG. 5. Neurochemical alterations in VAChT KD$^{HET}$ mice A. Extracellular ACh levels as determined by quantitative "low perfusion rate" microdialysis in frontal cortex and striatum. n=10 mice/genotype/brain region. B. KCl-stimulated release of ACh in striatum of freely-moving mice. Following 40 min of baseline collection of ACh, 60 mM (K$^+$) was infused through the microdialysis probe for 40, and artificial CSF was infused over the last 40 min of the experiment. N=7 mice/genotype. *$p<0.05$ from WT controls. C. Tissue ACh contents in frontal cortex (FC) and striatum (ST) of WT and KD$^{HET}$ mice measured by HPLC with electrochemical detection. FC: N=14 WT and 13 KD$^{HET}$ mice; ST: N=6 mice/genotype D. Striatal (ST) and hippocampal (HIP) tissue ACh levels assayed by chemiluminescent detection in wild-type (open bars) and VAChT KD$^{HET}$ (gray bars) mice (N=5). In all panes data are mean±SEM. *$p<0.05$ from wild-type controls.

To investigate the functional consequences of reduced VAChT expression, we first used brain microdialysis to establish extracellular levels of ACh in freely moving VAChT KD$^{HET}$ mice. Because all brain regions examined appeared to show similar reductions in VAChT expression, we chose to determine extracellular ACh levels in frontal cortex and striatum. Frontal cortex was selected because this brain region receives innervation from nucleus basalis and substantia innominata, areas known to be affected in Alzheimer's disease. Striatum was chosen because it contains the largest concentration of cholinergic nerve endings, and is therefore particularly suitable to evaluate possible decreases in extracellular ACh. The quantitative "low perfusion rate" microdialysis approach which allows precise determination of extracellular neurotransmitter (Gainetdinov et al. (2003) Dopaminergic supersensitivity in G protein-coupled receptor kinase 6-deficient mice. *Neuron* 38:291-303), revealed that levels of extracellular ACh were depressed by more than 35% in frontal cortex ($t(1,19)=2.642$, $p<0.016$) and by approximately 31% in striatum ($t(1,18)=2.560$, $p<0.020$) of VAChT KD$^{HET}$ mice (FIG. 5A). Next, by using the conventional microdialysis approach, we examined the dynamic responses to KCl-stimulated ACh release in the striatum. After establishing basal extracellular ACh levels, artificial CSF containing 60 mM (K$^+$) was perfused through the microdialysis probe over the next 40 min, and the probe was returned to normal artificial CSF for the remaining 40 min of the experiment (FIG. 5B). A repeated measures ANOVA revealed a significant main effect of time ($F(5,60)=31.541$, $p<0.001$) and a significant time by genotype interaction ($F(5,60)=7.502$, $p<0.001$). Bonferroni corrected pairwise comparisons showed genotype effects at 40 ($p<0.044$), 60 ($p<0.023$), and 80 min ($p<0.026$). Hence, both genotypes responded to KCl depolarization; however, stimulated release in KD$^{HET}$ striatum was reduced relative to that of the wild-type controls.

Since VAChT is responsible for sequestering ACh into secretory vesicles, we evaluated the effects of decreased VAChT expression on total ACh levels in brain tissue. When tissue concentrations of ACh were measured by HPLC-EC, levels in frontal cortex and striatum of VAChT KD$^{HET}$ mice were significantly increased by approximately 49% ($t(1,25)=4.082$, $p<0.001$) and 30% ($t(1,10)=3.408$, $p<0.007$), respectively, over that of the wild-type controls (FIG. 5C). These data were replicated in a complementary chemiluminescence assay in a separate group of mice for striatum and hippocampus (FIG. 5D; $p<0.05$). Moreover, VAChT KD$^{HOM}$ mice show an even larger increase in ACh content in the brain and this was statistically different from VAChT KD$^{HET}$ mice or wild-type mice (FIG. 6C $p<0.05$). This increase in ACh content for mutant mice cannot be attributed to an increase in ChAT activity (FIG. 6A), high-affinity choline transporter activation (FIG. 6D), or increased levels of expression of ChAT (FIG. 6B and FIG. 1E) or CHT1 (FIG. 1E). Whereas the mechanism of such an increase in total tissue ACh content it is not immediately apparent, it is important to emphasize that the functional "releasable" ACh pool seems to be decreased, as evidenced by in vivo microdialysis experiments and also by quantal analysis at the neuromuscular junction. Altogether these results demonstrate that a reduction of approximately 50% in the levels of VAChT expression in the brain results in a significant decrease in the release of ACh "in vivo," despite enhanced intracellular content of neurotransmitter. These observations suggest a complex relationship in the control of storage and release of ACh in CNS neurons.

Behavioral Evaluation.

After documenting normal performance of VAChT KD$^{HET}$ mice in tests of neuromuscular strength, but reduced cholinergic tone in the brain, we proceeded to evaluate performance of mutants in behavioral tasks reflecting CNS cholinergic function. VAChT KD$^{HET}$ mice were tested for performance in the step-down inhibitory avoidance task, a task that depends upon hippocampal and amygdala networks and may be sensitive to manipulations in central cholinergic function (Izquierdo et al. (1997) Memory formation: the sequence of biochemical events in the hippocampus and its connection to activity in other brain structures. *Neurobiol. Learn. Mem.* 68:285-316).

The step-down inhibitory avoidance apparatus was a 50×25×25 cm acrylic box whose floor consisted of a grid of parallel stainless steel bars 1 mm in diameter spaced 1 cm apart. A 10-cm$^2$ wide, 2-cm high, acrylic platform was placed in the center of the floor. Animals were placed on the platform and their latency to step down on the grid with all four paws was measured with an automatic device. In the training session, immediately after stepping down on the grid the animals received a 2.0-s, 0.3 mA, scrambled foot-shock. Retention test sessions were procedurally identical except that no foot-shock was given. The latency to step down during testing was taken as a measure of retention. A ceiling of 180 s was imposed in this measure, i.e., animals whose test latency was over than 180 s were counted as 180 s. Each animal was tested twice, once at 1.5 h after training, to measure short-term retention, and once at 24 h after training, to measure long-term retention (Izquierdo et al. (2002) Repetition of memories lost or never acquired. *Trends Neurosci.* 25:77-78; Lorenzini et al. (1996) Role of dorsal hippocampus in acquisition, consolidation and retrieval of rat's passive avoidance response: a tetrodotoxin functional inactivation study. *Brain Res.* 730:32-39). Since the variable being analyzed (step-down latency) does not follow a normal distribution, the data were analyzed by Mann-Whitney U or Kruskal-Wallis nonparametric tests followed by Duun's post-hoc comparisons where appropriated.

Figure 7:
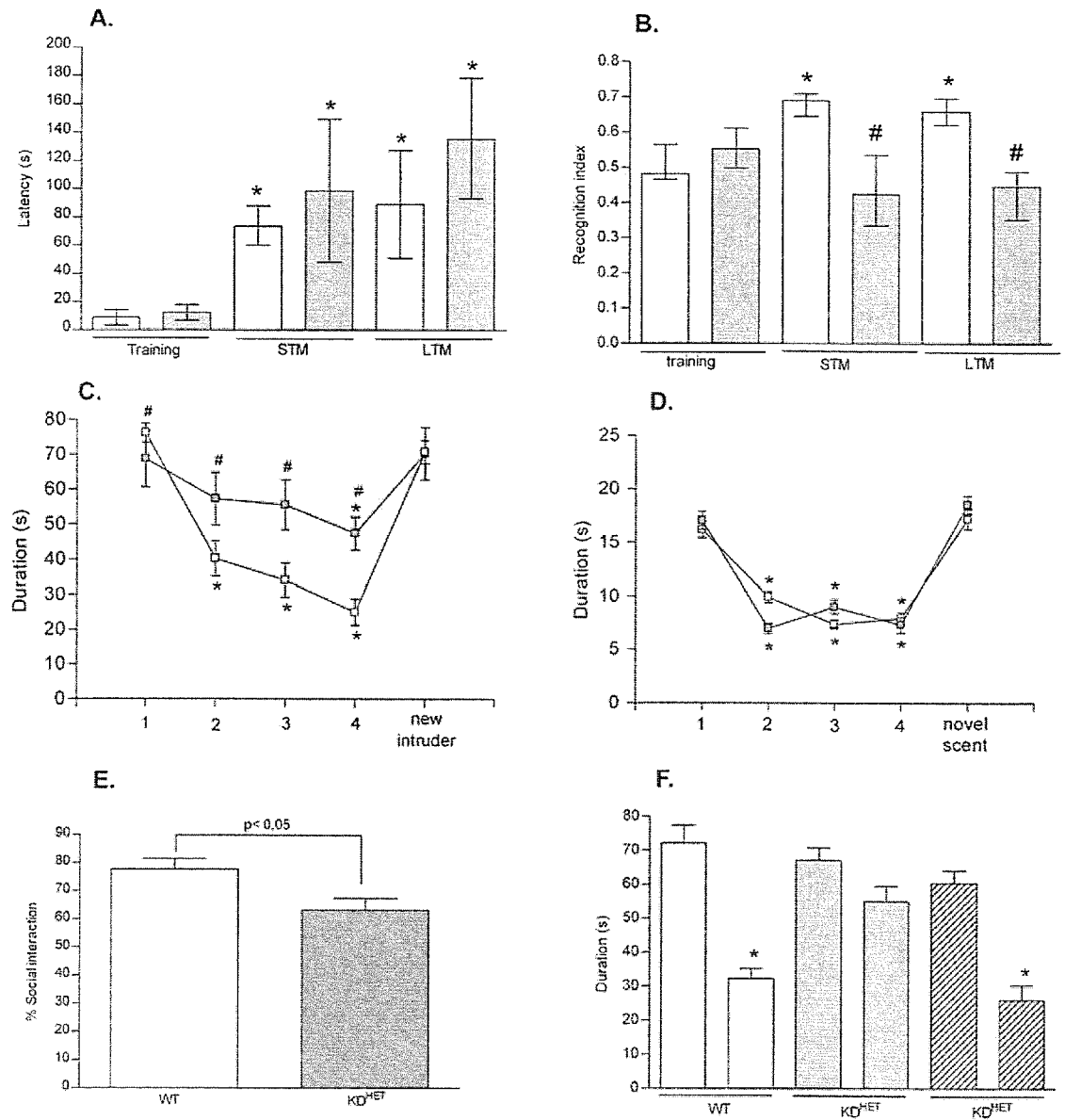
FIG. 7. Behavioral alterations of VAChT KD$^{HET}$ mice. A. Step-down inhibitory avoidance task. Retention test latency measured 90 min after training (STM) and again at 24 hours (LTM). Ordinates express median (interquartile range) test session latency, in seconds. Open bars present the performance of wild-type mice and shadowed bars represents that of VAChT KD$^{HET}$ mice (N=13-18 per group). *$p<0.05$ compared to training B. Object recognition test. Results are shown as median (interquartile ranges) recognition indexes of short-term (STM) and long-term (LTM) retention test trials. Clear bars represent data from wild-type mice and shadow bars are the data for VAChT KD$^{HET}$ mice. # indicates a significant difference from wild type $p<0.05$, N=12-18. * indicates $p<0.05$ compared to training C. Social memory of wild-type (open squares) and KD$^{HET}$ mice (gray squares) was measured as olfactory investigation during each of four successive 5 min trials with an inter-trial interval of 15 min. A fifth dishabituation trial depicts the response of mice to the presentation of a new intruder in a 5 min pairing, 15 min after the fourth trial. *p<0.05 compared to performance on the first trial within the genotype, #p<0.05 when compared to wild-type control mice; N=10-12. D. Olfactory function of wild-type and VAChT KD$^{HET}$ mice. Mice were presented a strawberry essence for 1 min in 4 sequential trials with an intertrial interval of 10 min. On the 5$^{th}$ trial, vanilla essence was presented. *p<0.05 from the first trial within genotype. No between group differences were observed. E. Social preference of wild-type (open bar) and VAChT KD$^{HET}$ mice. Only the percentage of exploration for the social stimulus is shown. F. Social memory of wild-type (open bars, N=14), VAChT KD$^{HET}$ (gray bars, N=14) and VAChT KD$^{HET}$ mice treated with galantamine (1 mg/kg, s.c.) 30 min prior to the first exposure to an intruder (hatched bars, n=8). The intruder is presented in each of two 5-min trials with an inter-trial interval of 30 min. *p<0.05 from the first trial within the genotype. Unless otherwise stated data are mean±SEM.

Both genotypes presented learning, as latency to step-down from the platform increased from 10-15 sec to approximately 80-100 sec after training. In parallel experiments, we determined in another cohort of mice that the unconditioned stimulus was essential for learning the task for both genotypes (not shown). VAChT KD$^{HET}$ performed as well as wild-type littermates on this task for short-term (1.5 hours after learning) and long-term memory (24 hours after learning), suggesting that this specific aspect of learning and memory is preserved in animals with mild-decrease in cholinergic tone (FIG. 7A).

A second test for memory was used to evaluate the performance of mutant mice, based on the ability to discriminate novel objects. In the object recognition task, mice explore two objects and after a latency of 1.5 or 24 hours they are presented with one of the familiar objects and a non-familiar object. All animals were given a single 5 min habituation session with no objects in the open-field arena (as described above). Twenty-four hours after habituation, training was conducted by placing individual mice for 5 min into the field, in which two identical objects (objects A1 and A2; Duplo Lego toys) were positioned in two adjacent corners, 10 cm from the walls. A minimum of 30 sec exploration time for objects was allowed in this first exposure. In a short-term memory (STM) test given 1.5 h after training, the mice explored the open field for 5 min in the presence of one familiar (A) and a novel (B) object. All objects presented similar textures, colors, and sizes, but distinctive shapes. A recognition index calculated for each animal was expressed by the ratio $T_B/(T_A+T_B)$ ($T_A$=time spent exploring the familiar object A; $T_B$=time spent exploring the novel object B). Between trials the objects were washed with 10% ethanol solution and air-dried. In a long-term memory (LTM) test given 24 h after training, the same mice explored the field for 5 min in the presence of familiar object A and a novel object C. Recognition memory was evaluated as for short-term memory test. Exploration was defined as sniffing or touching the object with nose and/or forepaws (de Lima et al. (2005) Selegiline protects against recognition memory impairment induced by neonatal iron treatment. *Exp. Neurol.* 196:177-183). Data for recognition indexes are expressed as median (interquartile ranges). Comparisons among groups were performed using a Kruskal-Wallis analysis of variance and Mann-Whitney U-tests. Recognition indexes within individual groups were analyzed with Wilcoxon tests.

Initial exploration time for two objects was identical for both genotypes indicating that they both show preference for novelty (not shown). However, whereas wild-type mice presented a significant increase in the exploration of the unfamiliar object, mutant mice performed poorly compared to wild-type mice in their ability to remember the familiar object 1.5 or 24 hours after learning (FIG. 7B, p<0.05, Kruskal-Wallis analysis of variance and Mann-Whitney U-tests, N=12-18). Thus, VAChT KD$^{HET}$ mice appear to have a cognitive deficit that is important for behavior in this test.

Recognition of a familiar conspecific is the basis of several social interactions, including hierarchical social relationship and mate choice (Winslow et al. (2004) Neuroendocrine basis of social recognition. *Curr. Opin. Neurobiol.* 14:248-253). There is evidence for the participation of nicotinic and muscarinic central systems in social recognition in rodents (Prediger et al. (2006) Pilocarpine improves olfactory discrimination and social recognition memory deficits in 24 month-old rats. *European Journal of Pharmacology* 531:176-182; van Kampen et al. (2004) AR-R 17779 improves social recognition in rats by activation of nicotinic alpha(7) receptors. *Psychopharmacology* 172:375-383; Winslow et al. (1995) Cholinergic modulation of a decrement in social investigation following repeated contacts between mice. *Psychopharmacology (Berl)* 121:164-172) and social recognition deficits may relate to cholinergic decline in a mouse model of AD (Ohno et al. (2004) BACE1 Deficiency Rescues Memory Deficits and Cholinergic Dysfunction in a Mouse Model of Alzheimer's Disease. *Neuron* 41:27-33). We evaluated social interactions for VAChT KD$^{HET}$ mice in a habituation-dishabituation paradigm using a mouse intruder (Choleris et al. (2003) An estrogen-dependent four-gene micronet regulating social recognition: a study with oxytocin and estrogen receptor-alpha and -beta knockout mice. *Proc. Natl. Acad. Sci. U.S.A.* 100:6192-6197). Mice were housed in individual cages in a quiet room for 4 days to establish territory dominance. Swiss juvenile male mice were used as the intruder. To test for social interaction, the intruder was placed inside a transparent acrylic chamber containing several holes and introduced into the test cage exactly as described (Choleris et al., 2003, supra). Time spend sniffing was measured as the amount of time that VAChT KD$^{HET}$ mice or wild-type littermates spent poking their noses into the holes of the chamber. Initially, the subject tested (wild-type or VAChT KD$^{HET}$ mice) was exposed to an empty acrylic chamber for 10 min and subsequently this chamber was exchanged by one containing the intruder for 5 min. The entire procedure was repeated 4 times. After the $4^{th}$ exposure to the same intruder, a novel intruder was added to the acrylic chamber. The experiment was videotaped and a trained researcher, blind to genotype, evaluated time spent sniffing in each condition.

A second experiment consisted of exposing the subject to the same intruder twice with an inter-trial interval of 30 min. The standard measure for the statistical analysis in social recognition tests was the time spent exploring the juvenile mice. To evaluate the contribution of acute cholinergic deficits, saline or 1 mg/kg galantamine (s.c.) was injected 30 min before beginning of the tests.

For evaluation of sociability we followed the protocol described by (Kwon et al. (2006) Pten regulates neuronal arborization and social interaction in mice. *Neuron* 50:377-388). Test was done in a three-chambered apparatus (15×90×18.5 cm divided into three chambers of 15×29 cm separated by dividers with a central 3.8×3.8 cm door) that offers the subject a choice between a social stimulus and an inanimate target. In the habituation session, mice were allowed to explore the entire box for 10 min. Subsequently, mice stayed 5 min in the center and then were allowed to interact with an empty cage in one chamber versus a caged social target in opposite chamber for 10 min. Social and non-social stimuli were varied among the chambers and the box was cleaned between tests. Results are presented as percentage of total exploration time.

Two tests to evaluate the olfactory response of the mice were conducted (Bielsky et al. (2005) The v1a vasopressin receptor is necessary and sufficient for normal social recognition: a gene replacement study. *Neuron* 47:503-513; Ferguson et al., 2000). The first consisted in measuring the time that both genotypes took to find a candy located on the surface of bedding or hidden within the bedding (Ferguson et al. (2000).

Social amnesia in mice lacking the oxytocin gene. *Nat. Genet.* 25:284-288). The second test investigated whether VAChT KD$^{HET}$ mice presented olfactory habituation and discrimination. Experiments were performed 7 days after completing the social recognition tests in the same groups of mice. For this test a microtube, with a piece of cotton containing 10 µl of strawberry essence was presented to mice four times for 1 minute with a 10 minutes intertrial interval. On the 5$^{th}$ trial, the microtube was exchanged with one containing vanilla essence. The significance of differences between the groups was determined by Student's t test or two-way ANOVA, and post-hoc Bonferroni test was performed when appropriate. Changes across trials were assessed with repeated-measures ANOVA with Bonferroni's post-hoc analysis.

Wild-type control mice showed extensive exploration of the intruder during first contact (e.g. sniffing). This response decreased with subsequent exposure to the same juvenile (F(4,11)=60.93, p<0.01), indicating that wild-type control mice readily habituated to the conspecific (FIG. 7C). Hence, after 4 exposures to the same juvenile, wild-type mice explored the intruder only one-third of the time compared to the time in the initial exploration. Upon changing to an unfamiliar mouse, wild-type animals showed a renewed interest in investigation, and explored the new mice as much as in the first contact (FIG. 7C). These results indicate that lack of interest in exploring the first intruder upon recurring exposure was not attributable to lack of motivation, but appears to be due to habituation (i.e. learning). Exploration of the intruder mice by VAChT KD$^{HET}$ mice on the first contact was slightly less than that observed for wild-type animals (p<0.05, Two-way ANOVA with Bonferroni post-hoc). Upon subsequent exposures, VAChT KD$^{HET}$ mice show statistically significant differences in exploration of the intruder mice as compared to wild-type mice (p<0.001, Two-way ANOVA with Bonferroni post-hoc). In sharp contrast to wild-type littermates, VAChT KD$^{HET}$ mice failed to habituate to the juvenile intruder in the subsequent exposures after the initial contact and only after the 4$^{th}$ contact there was a significant difference in exploratory behavior compared to the first encounter (F(4,10)= 5.293, FIG. 7C). Introduction of an unfamiliar mice led VAChT KD$^{HET}$ mice to increase their exploration, indicating that the decrease in exploration during the 4$^{th}$ exposure for the first intruder was not due to non-specific effects, such as physical exhaustion or motivation.

One possible explanation for the inability of VAChT KD$^{HET}$ mice to habituate to a conspecific is that mutant mice have olfactory deficits. In a control experiment, we evaluated olfactory responses in these mice. Both wild-type and VAChT KD$^{HET}$ mice showed similar abilities in finding a hidden food reward (not shown), suggesting that the differences observed in social recognition do not relate to deficits in olfactory function. In addition, wild-type and VAChT KD$^{HET}$ mice habituated to a test odor (WT F(4,6)=11.35 and VAChT KD$^{HET}$ mice F(4,6)=18.11, p<0.05 by repeated measures ANOVA). There were no differences between the two genotypes in olfactory habituation or in their ability to discriminate between two test odors (FIG. 7D).

A second possibility to explain the deficit in social habituation is that VAChT KD$^{HET}$ mice are more social than wild-type mice, i.e. they prefer the company of intruder mice more than wild-type mice. This would be the contrary of the autistic like behavior found in PTEN mutant mice (Kwon et al. (2006) Pten regulates neuronal arborization and social interaction in mice. *Neuron* 50:377-388). To specifically test this possibility, we evaluated the choice of wild-type and VAChT KD$^{HET}$ mice for a social (an adult mice in an acrylic cage that allowed minimum tactile exploration but allowed olfactory exploration) against a non-social stimuli (an identical acrylic cage which was never presented to the mice). This experiment was done in specially designed boxes containing two separate rooms where the mice had to enter to explore social or non social target (Kwon et al. (2006), supra). As expected from the previous experiment both genotypes had a stronger preference for the social against the non-social stimuli (FIG. 7E), however VAChT KD$^{HET}$ mice expended significantly less time with the social stimuli and consequently more time with the non-social stimuli than wild-type control mice (p<0.05, Student's t Test). Therefore, increased social preference of VAChT KD$^{HET}$ mice cannot explain the lack of habituation observed in the social recognition test. If anything, the data indicate that VAChT KD$^{HET}$ mice are less social than control mice.

Figure 8:
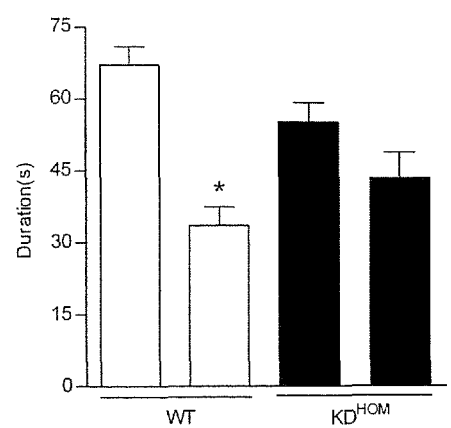
FIG. 8. The deficit in social recognition memory was also observed in a small number of VAChT KD$^{HOM}$ mice studied.

The results above suggest that VAChT KD$^{HET}$ mice have a deficit in social memory. This phenotype could be a consequence of decreased ACh release, or it could result from adaptative changes in brain neurochemistry during development, in response to the decreased expression levels of VAChT. If the deficits in social recognition are related to decreased acetylcholine output, acute inhibition of cholinesterase, which preserves ACh in the synapse, might rescue the phenotype. Therefore, we retested mice in the social memory task using a paradigm that allowed us to treat mice with a cholinesterase inhibitor prior to the experiment. The social recognition memory lasted at least 30 min, as wild-type mice exposed to an intruder for 5 min twice, with an inter-trial interval of 30 min, explore the intruder significantly less in the second exposure (F (5,70)=17.21, p<0.001) (FIG. 7F). In contrast, there was no difference for VAChT KD$^{HET}$ mice in the first and second exposure to intruder mice with this protocol (FIG. 7E). We repeated these experiments after injecting mice with either saline or galantamine (FIG. 7F). The dose of galantamine used (1 mg/kg s.c.) has been shown to be effective in improving cholinergic function in mice (Csernansky et al. (2005) Cholinesterase inhibitors ameliorate behavioral deficits induced by MK-801 in mice. *Neuropsychopharmacology* 30:2135-2143), and it was sufficient to improve the performance of VAChT KD$^{HET}$ in this social recognition task (FIG. 7F). Injection of saline had no effect on the performance of wild-type or VAChT KD$^{HET}$ mice, ruling out that prior manipulation of mice affected the outcome of these experiments (not shown). In addition, galantamine did not alter the response of wild-type mice (not shown). It should be noted that the deficit in social recognition memory was also observed in a small number of VAChT KD$^{HOM}$ mice studied with an identical protocol (FIG. 8), thus confirming this phenotype for the two mutant genotypes. Hence, it appears that VAChT KD$^{HET}$ mice have a deficit in social memory due to decreased cholinergic tone.

Discussion. It has been demonstrated that several putative mRNA species exist for VAChT, although V1 is predominant in cholinergic tissues (Bejanin et al. (1994) A unique gene organization for two cholinergic markers, choline acetyltransferase and a putative vesicular transporter of acetylcholine. *J. Biol Chem.* 269:21944-21947). In the present experiments, we show that VAChT KD$^{HET}$ and KD$^{HOM}$ mice have reduced levels of this major VAChT mRNA, whereas an increase in a less common mRNA for VAChT was detected, suggesting the existence of a compensatory mechanism in mutant mice. The open reading frame of VAChT is within the first intron of the ChAT gene. Interestingly, we detected no changes in ChAT mRNA levels in all CNS regions investigated, even though CHAT and VAChT transcripts might be, under certain conditions, co-regulated (Eiden (1998) The cholinergic gene locus. *J. Neurochem.* 70:2227-2240). In vertebrates, regulation of the cholinergic gene locus expression is complex, ChAT and VAChT specific mRNAs can be produced either from different promoters or by alternative RNA splicing (Oda (1999) Choline acetyltransferase: the structure, distribution and pathologic changes in the central nervous system. *Pathol. Int.* 49:921-937).

In addition to the decrease in VAChT transcript, we detected a 45% reduction in VAChT protein levels in several CNS regions in VAChT $KD^{HET}$ mice, whereas the reduction of VAChT protein levels in homozygous mutant mice was 65-70% of that found in wild-type littermates. Therefore, the data indicate that protein levels of VAChT follow close the reduction of the major VAChT mRNA species.

To evaluate how a decrease in VAChT levels affects transmitter release we examined quantal secretion of ACh at the neuromuscular junction. Surprisingly, we observed relatively mild alterations in the distribution of quantal sizes in VAChT $KD^{HET}$ mice. A robust change in quantal size distribution for VAChT $KD^{HOM}$ mice was detected, however a very pronounced decrease in the frequency of MEPPs was also observed. This decrease in MEPP frequency is not the result of alterations in the readily releasable pool of vesicles. It seems also unlikely that the alteration in MEPP frequency is the result of decreased exocytosis, endocytosis and total pool of vesicles, as FM1-43 experiments have shown no difference in these parameters between wild-type and VAChT $KD^{HOM}$ mice. We hypothesized that if in synapses the number of copies of VAChT per synaptic vesicles is low (Parsons et al. (1993) Acetylcholine transport, storage, and release. *Int. Rev. Neurobiol.* 35:279-390; Van der Kloot (2003) Loading and recycling of synaptic vesicles in the Torpedo electric organ and the vertebrate neuromuscular junction. *Prog. Neurobiol.* 71:269-303), a reduction in VAChT abundance could result in electrophysiological "silent" vesicles, and thus a decrease in MEPP frequency. Prior experiments have demonstrated that overexpression of VAChT in immature Xenopus spinal neurons increases not only the amplitude but also the frequency of miniature excitatory post-synaptic currents (Song et al. (1997) Expression of a putative vesicular acetylcholine transporter facilitates quantal transmitter packaging. *Neuron* 18:815-826), indicating that at least under certain conditions VAChT expression levels can affect electrophysiological detection of exocytosis. Similarly, in Drosophila mutants with decreased neuromuscular expression of the vesicular glutamate transporter, there are major deficits in frequency of miniature end-plate currents, but no alterations in quantal size (Daniels et al. (2006) A single vesicular glutamate transporter is sufficient to fill a synaptic vesicle. *Neuron* 49:11-16). Remarkably, VAChT phosphorylation by PKC affects its trafficking to secretory vesicles, suggesting that alterations in VAChT expression in synaptic vesicles could occur physiologically (Krantz et al. (2000) A phosphorylation site regulates sorting of the vesicular acetylcholine transporter to dense core vesicles. *J. Cell Biol.* 149:379-396).

The results herein with VAChT mutant mice also indicate that synaptic vesicle exocytosis is not altered by decreased levels of the transporter; in this regard these results agree with similar observations in VMAT2-deficient mice (Croft et al. (2005) Normal biogenesis and cycling of empty synaptic vesicles in dopamine neurons of vesicular monoamine transporter 2 knockout mice. *Mol. Biol. Cell* 16:306-315), that also present no deficits in monoaminergic vesicle exocytosis. Nonetheless, the data show that VAChT $KD^{HET}$ mice have mild changes in ACh release at the neuromuscular junction, whereas VAChT $KD^{HOM}$ mice have a more profound deficit in transmitter release.

Analysis of neuromuscular function in the three genotypes corroborated these electrophysiological data. VAChT $KD^{HET}$ mice performed as well as wild-type mice in tests of motor function, whereas VAChT $KD^{HOM}$ mice were significantly impaired in grip strength and ability to hold their weight. Importantly, the deficit in grip strength could be ameliorated by prior treatment of mutant mice with cholinesterase inhibitors. The effect of pyridostigmine, which is used to treat myasthenia, is of particular importance, as it indicates that a peripheral cholinergic deficit due to alteration in neuromuscular transmission is the cause of neuromuscular dysfunction.

Investigation of VAChT KD mice on the rotarod, a task that depends upon motor learning and physical endurance, reveals that VAChT $KD^{HET}$ are slower to learn this motor task than wild type control mice, but the former are able to reach the same level of performance in time. In contrast, VAChT $KD^{HOM}$ mice are significantly impaired and never improve their performance. That VAChT $KD^{HOM}$ mice have limited capacity for exercise is clearly observed on the treadmill, indicating that performance of the homozygous mutants on the rotarod reflects their inability to maintain prolonged physical activity. These results suggest that VAChT $KD^{HOM}$ mice may provide a model to study the consequences of markedly reduced ACh release on neuromuscular function, as observed in certain types of congenital pre-synaptic myasthenia (Ohno et al. (2001) Choline acetyltransferase mutations cause myasthenic syndrome associated with episodic apnea in humans. *Proc. Natl. Acad. Sci. U.S.A.* 98:2017-2022).

In contrast, we were unable to detect any alteration in neuromuscular function in VAChT $KD^{HET}$ mice. Release of ACh accompanied the reduction of protein expression in the brain for VAChT $KD^{HET}$ mice, and both basal and stimulated extracellular levels were affected. This decrease in ACh release appears to be related to the reduction of VAChT expression, as ChAT activity was not decreased in these mutants. Overall, the approximately 45% reduction in VAChT expression appears to decrease ACh secretion to a similar extent in the brain. Unexpectedly, tissue ACh was significantly increased in several brain regions from VAChT $KD^{HET}$ and also for VAChT $KD^{HOM}$ mice, indicating a previously unrecognized connection between ACh storage, non-vesicular ACh pools and tissue content. Molecular mechanisms responsible for this increased tissue ACh content have not been uncovered yet, but it does not seem to be due to altered ChAT activity or high affinity choline uptake. It is interestingly that pharmacological experiments with vesamicol an inhibitor of VAChT, have revealed a similar relationship, whereby decreased secretion of ACh leads to accumulation of intracellular transmitter during nerve stimulation (Collier et al. (1986) Acetylcholine synthesis and release by a sympathetic ganglion in the presence of 2-(4-phenylpiperidino)cyclohexanol (AH5183). *J. Neurochem.* 46:822-830).

Whereas VAChT $KD^{HET}$ mice present only mild defects in neuromuscular neurotransmission, there is a relatively larger deficiency in central ACh release in vivo. Neuromuscular transmission has a high safety margin, and neuromuscular weakness is not observed until a significant proportion of neuromotor units are compromised (Paton et al. (1967) The margin of safety of neuromuscular transmission. *J. Physiol.* 191:59-90; Waud et al. (1975) In vitro measurement of margin of safety of neuromuscular transmission. *Am. J. Physiol.* 229:1632-1634). Therefore, it is reasonable to envision that a partial decrease in VAChT expression will cause more profound consequences on cholinergic transmission in the brain, where a relatively small number of synaptic vesicles (100-200 vesicles) need to be constantly recycled and refilled with neurotransmitter. In contrast, at neuromuscular synapses, there is a very large population of vesicles; fast refilling of vesicles may not be as crucial for neurotransmission at the neuromuscular junction as it is for brain synapses, at least under low neuromuscular demand.

The VAChT KD$^{HET}$ mice present a unique opportunity to investigate the consequences of homogeneous decrease of ACh tone in cognitive tasks, as the results show that these mice represent a model of moderate, predominantly central cholinergic dysfunction. We observed no deficits in performance of VAChT KD$^{HET}$ mice in the step-down inhibitory avoidance test. A number of experiments have demonstrated that inhibition of nicotinic and muscarinic central receptor activity can affect performance of rats in this paradigm (Barros et al. (2002) Modulation of working memory and of long- but not short-term memory by cholinergic mechanisms in the basolateral amygdala. *Behav. Pharmacol.* 13:163-167), indicating an important cholinergic contribution for performance in this test. It is likely that the reduction of cholinergic function in VAChT KD$^{HET}$ was below the threshold for detecting a learning or memory impairment for this task. This result supports the notion that ACh participates, but is not essential, for some hippocampal-dependent paradigms of learning and memory (Parent et al. (2004) Septohippocampal acetylcholine: involved in but not necessary for learning and memory? *Learn. Mem.* 11:9-20).

Interestingly, VAChT KD$^{HET}$ mice performed worse than wild-type mice in an object recognition test, suggesting that even mild decline of cholinergic function can affect cognitive processes required for this task. Indeed, rats treated with 192 IgG-saporin, which leads to cholinergic degeneration in the basal forebrain, also present object recognition deficits (Paban et al. (2005) Time course of behavioral changes following basal forebrain cholinergic damage in rats: Environmental enrichment as a therapeutic intervention. *Neuroscience* 132: 13-32), and object recognition alterations are observed in certain mouse models of AD (Dewachter et al. (2002) Neuronal deficiency of presenilin 1 inhibits amyloid plaque formation and corrects hippocampal long-term potentiation but not a cognitive defect of amyloid precursor protein (V717I) transgenic mice. *J. Neurosci.* 22:3445-3453). It is likely that VAChT KD$^{HET}$ present such deficits because they have impairments in ability to learn or remember the intricate cues necessary for discriminating the novel object.

Our data also revealed an important role of cholinergic tone in recognition of mouse conspecifics. In these experiments, the KD$^{HET}$ mice explore unfamiliar mice, however their preference for a social stimuli is somewhat decreased compared to wild-type mice. Nonetheless, the mutant mice are not socially deficient; but they clearly are impaired in remembering intruder mice when compared to wild-type mice. Absence of deficits in olfactory discrimination in VAChT KD$^{HET}$ mice supports the notion that the decreased social memory is due to cognitive impairments, rather than just incapacity to process olfactory cues. An important role of cholinergic tone in social recognition is supported by reversal of this phenotype in mice treated with a cholinesterase inhibitor and by the fact that VAChT KD$^{HOM}$ mice also present a significant deficit in social recognition.

Social memory in rodents depends upon the activity of vasopressin on VIA receptors in the lateral septum (Bielsky et al. (2005) The v1a vasopressin receptor is necessary and sufficient for normal social recognition: a gene replacement study. *Neuron* 47:503-513) and on oxytocin (Bielsky et al. (2004) Oxytocin, vasopressin, and social recognition in mammals. *Peptides* 25:1565-1574; Ferguson et al. (2000). Social amnesia in mice lacking the oxytocin gene. *Nat. Genet.* 25:284-288; Winslow et al. (2004) Neuroendocrine basis of social recognition. *Curr. Opin. Neurobiol.* 14:248-253). However, central muscarinic and alpha7 nicotinic receptors have also been suggested to play a role in social memory (Prediger et al. (2006) Pilocarpine improves olfactory discrimination and social recognition memory deficits in 24 month-old rats. *European Journal of Pharmacology* 531:176-182; van Kampen et al. (2004) AR-R 17779 improves social recognition in rats by activation of nicotinic alpha(7) receptors. *Psychopharmacology* 172:375-383; Winslow et al. (1995) Cholinergic modulation of a decrement in social investigation following repeated contacts between mice. *Psychopharmacology (Berl)* 121:164-172), indicating a potential mechanism for ameliorating social memory deficits in response to cholinergic decline. Our observations support the notion that reduced cholinergic tone in AD mouse models can indeed cause deficits in social memory. However, based on somewhat similar impairments found in the object and social recognition tasks, it is possible that mild cholinergic deficits may cause a more general memory deficit for recognizing previously learned complex cues whether social or not. Future detailed investigations will be necessary to further define the specific type of cognitive processing affected by cholinergic deficits in these mutants. Such studies in mouse models of reduced cholinergic tone may be particularly informative for understanding the contribution of cholinergic decline to specific behavioral alterations observed in certain pathologies of the CNS and even during physiological aging (Cummings (2004) Alzheimer's disease. *N. Engl. J. Med.* 351:56-67).

Additionally, data on the VAChT KD mice indicate that their autonomic nervous system is compromised. The VAChT KD mice suffer from progressive cardiac heart failure with alterations in cardiac physiology and circulation physiology, named alterations in heart rate, arterial pressure, etc. (data not shown).

In conclusion, we have generated a novel animal model to study the impact of decreased VAChT expression on peripheral and central ACh neurotransmission and function. The present results illuminate the role of VAChT in vesicular ACh release and reveal that deficits in VAChT-mediated filling of synaptic vesicles may have important behavioral consequences. Furthermore, these observations support an important role of ACh in cognitive processes involved in object and social recognition and memory. In this respect, a decrease in VAChT expression is much less tolerated than a decrease in CHAT activity, a parameter that is used extensively to evaluate cholinergic deficits in AD.

Example 2

Figure 9:
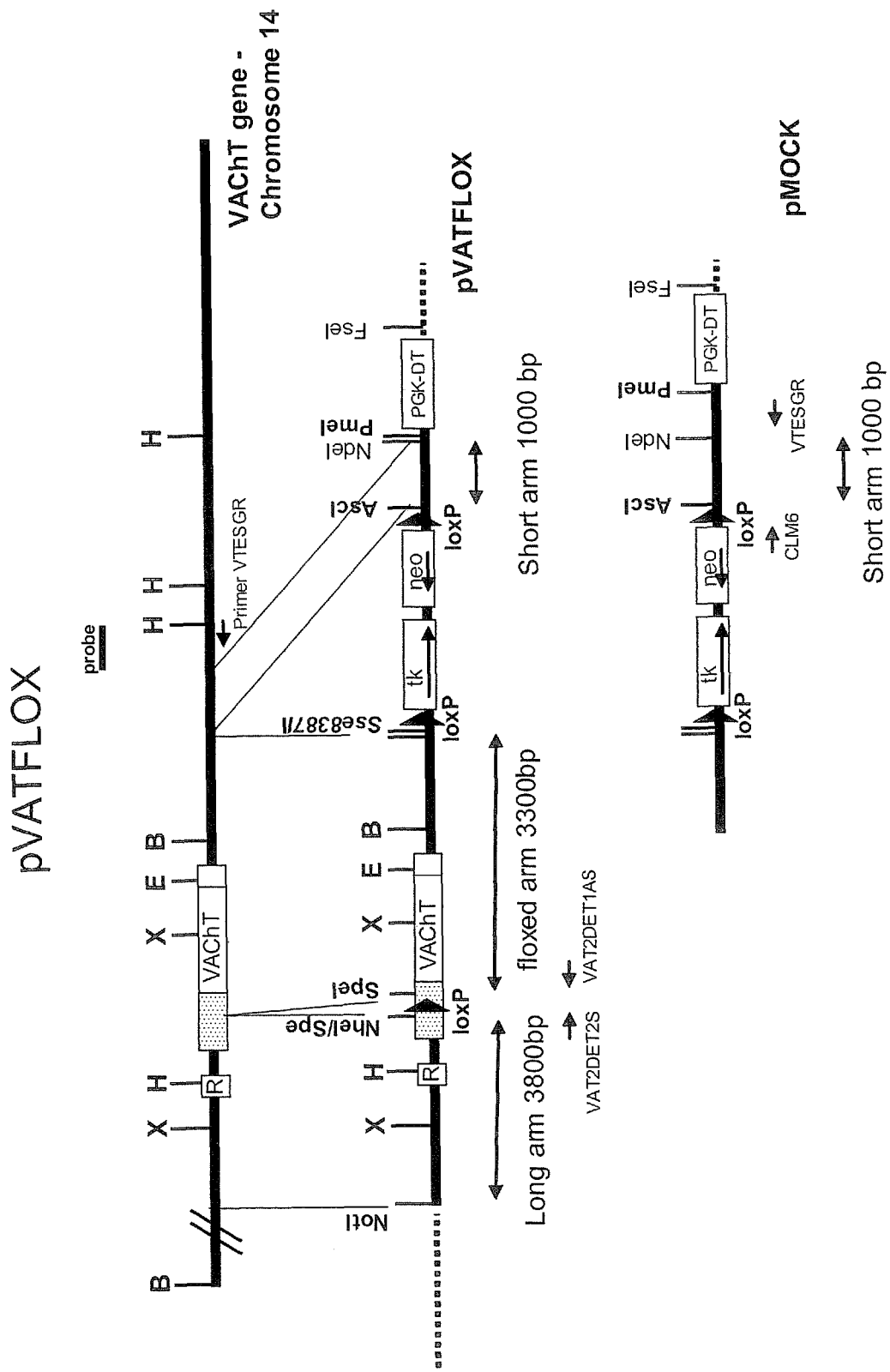
FIG. 9. Schematic illustration of a targeting vector to generate "FLOXED" VAChT mice for tissue specific deletion of the VAChT Gene.

Targeting Vector to Generate FLOXED VAChT Mice for Tissue-Specific Deletion of the VAChT Gene The rationale for developing a conditional or tissue specific knockout of VAChT is based on the assumption that mice null for this transporter would not survive, due to impaired breathing. To achieve conditional or tissue specific gene inactivation, the VAChT gene is replaced, by homologous recombination, with a floxed VAChT gene (see FIG. 9). The targeting vector was used to generate chimeric mice using standard transgenic techniques. Germ-line transmission was obtained used to generate a colony of loxP-VAChT mice.

These animals will be used to generate mouse lines with conditional or tissue-specific deletion of VAChT by standard mouse breeding protocols. A first candidate Cre-mouse that we propose to use for brain specific inactivation express Cre under the control of the CaMKIIα promoter. This transgenic line, on a C57BL/6 background, expresses Cre in the forebrain, and therefore is expected to mediate recombination in cholinergic neurons that project to the cortex and hippocampus. Other mice expressing the recombinase Cre that we propose to use are the mGluR2 described below, the kainate receptor 1-Cre mice and the MLC-Cre3 mice. Importantly, due to the nature of loxP-VAChT animals, availability of novel Cre-mice with site specific expression of Cre will allow more restricted inactivation of VAChT.

A key feature to develop tissue specific deletions is that the genetically modified mice present no deficit on VAChT expression prior to Cre mediated recombination. In case the line we have developed presents no alteration in VAChT expression prior to Cre-induced recombination, we will start breeding this mouse line with distinct Cre mice. Alternatively, it may be necessary to breed the loxP-VAChT line to Cre-mice (expressing Cre ubiquitously) by a few generations, in order to remove the Neo-resistance cassette but preserving the VAChT gene, in case the cassette interferes with VAChT expression. Offspring carrying the proper genotype will be crossed to C57BL/6 mice to obtain founder mice that have lost the Neo-cassette and also Cre. It is expected that we should obtain founder mice in which the Neo-cassette is removed, without deletion of the VAChT gene. These mice will then be bred to Cre mice that express the enzyme under the control of the CaMKIIα promoter.

Figure 10:
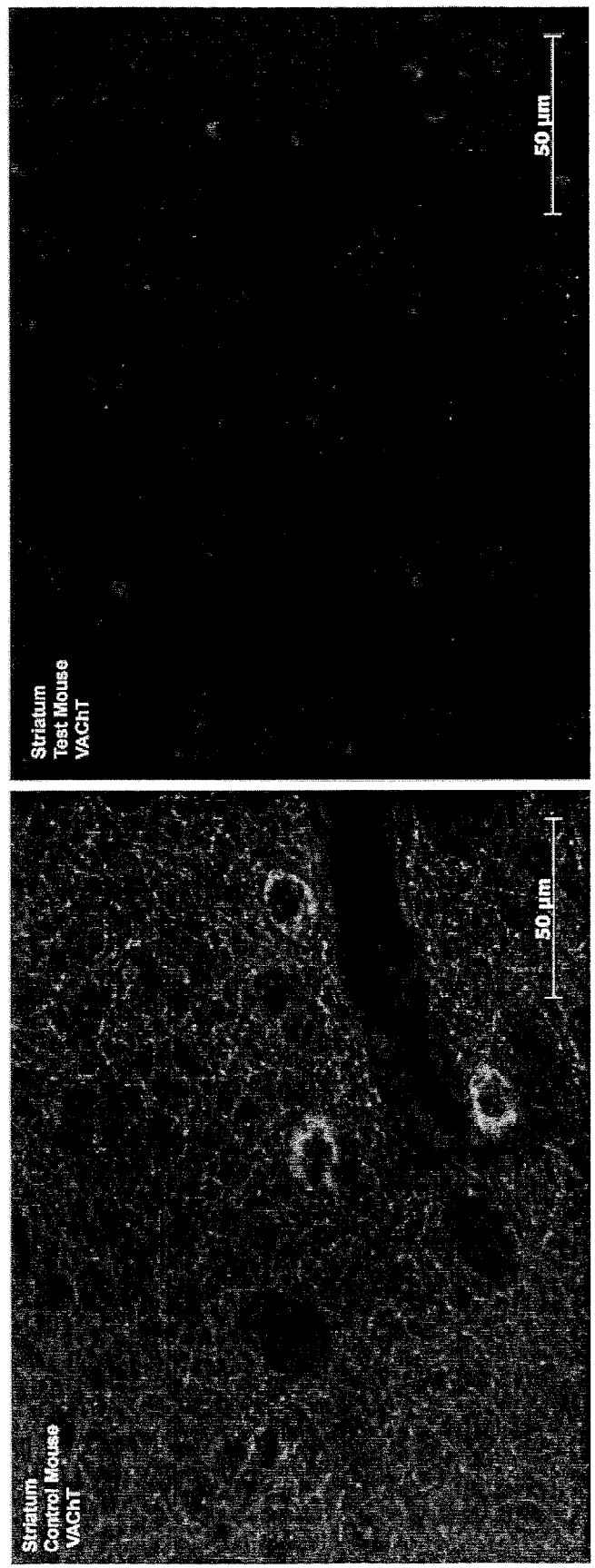
FIG. 10. Immunofluorescence images of a brain region from wild-type control mice (left) and of a VAChT flox/CamKinase II Cre mice (Right). In green is the immunoreactivity for VAChT detected with an specific VAChT antibody and a fluorescent secondary antibody labeled with Alexa 488 and in blue is the nuclei of neurons labeled with the fluorescent marker DAPI. Note that brain from VAChT flox/CamKinase II Cre mice has no detected levels of VAChT in the forebrain.
Figure 11:
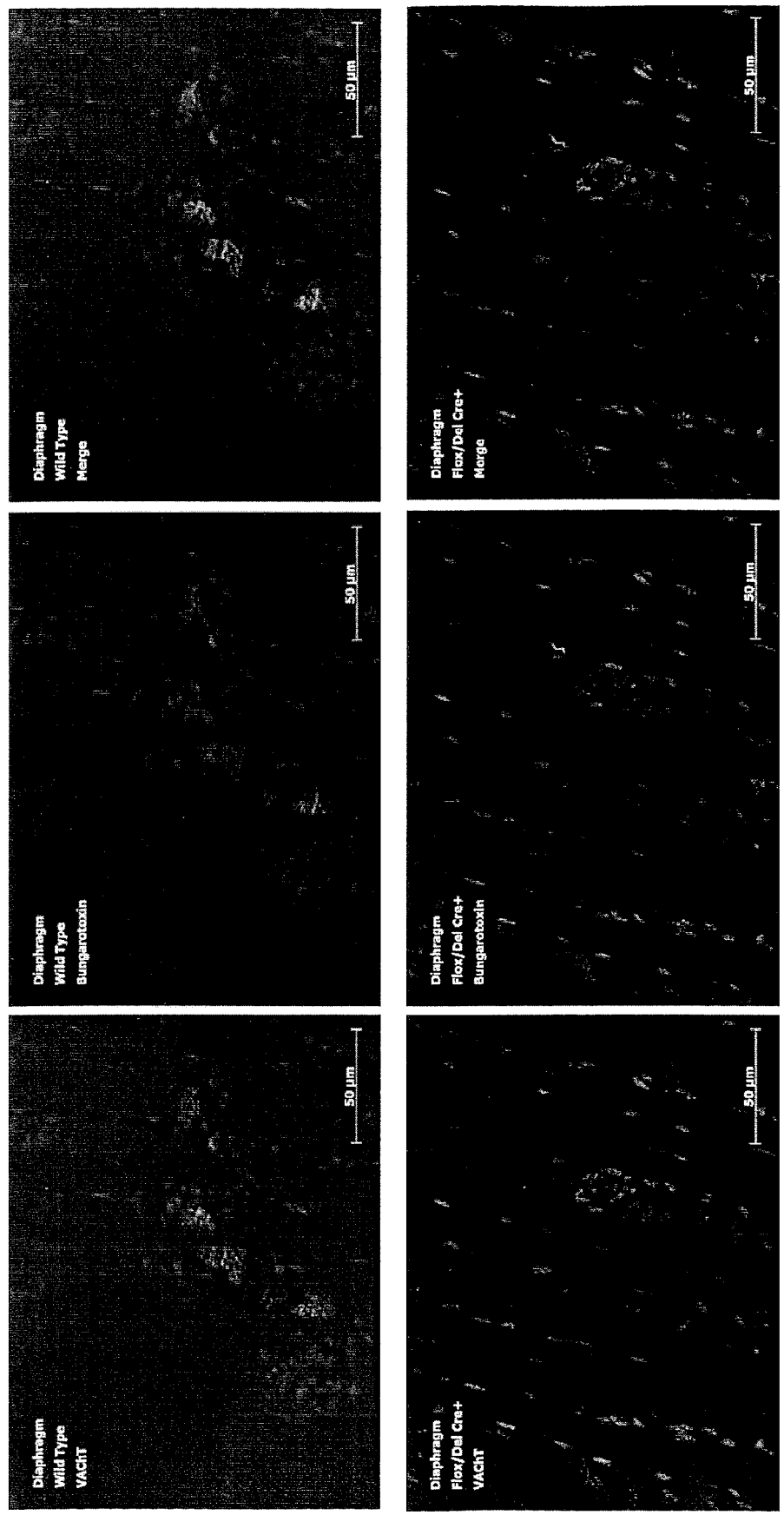
FIG. 11. Immunofluorescence images of the neuromuscular junction of wild-type control mice (top) and of a VAChT flox/CamKinase II Cre mice (bottom). In green is the immunoreactivity for VAChT detected with an specific VAChT antibody and a fluorescent secondary antibody labeled with Alexa 488, in blue is the nuclei of cells labeled with the fluorescent marker DAPI and in red is shown nicotinic receptors labeled with fluorescent bungarotoxin. Note that VAChT levels detected with green label are similar in top and bottom images suggesting that there is no neuromuscular alteration in VAChT expression in the neuromuscular junction.

We used VAChT flox mice and bread them to Calcium Calmodulin Kinase II Cre mice to delete the VAChT gene in brain regions. The new allele lost the VAChT gene due to Cre recombination of loxP sites in the brain, thus generating a brain specific VAChT Knockout. Mice were born normal (compared to wild type littermates) but after two weeks they lose weight become immobile and fail to feed. Mice die with postural defects, similar to those found in cerebral palsy, after 2-7 weeks. These mutant mice do not have expression of VAChT in the forebrain as detected by immunoblot and immunofluorescence (FIG. 10). Immunofluorescence images of the neuromuscular junction of wild-type control mice and of a VAChT flox/CamKinase II Cre mic suggested that there is no neuromuscular alteration in VAChT expression in the neuromuscular junction (FIG. 11).

Figure 12:
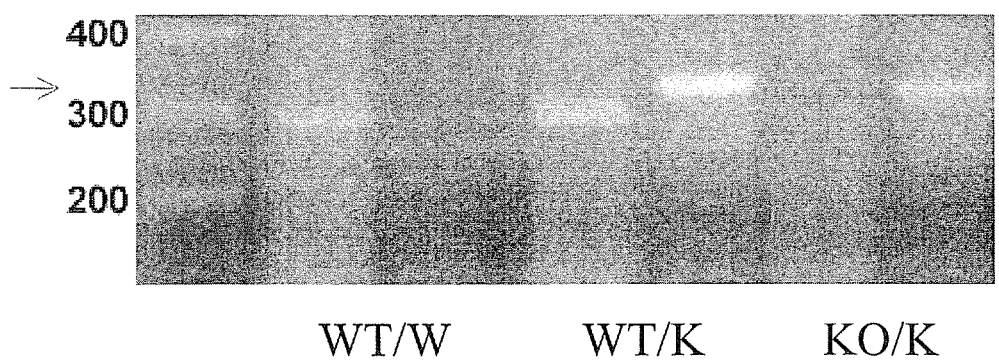
FIG. 12. A two-round PCR detects the mutant KO allele. WT allele 300 bp, mutant allele 330 bp indicated by the arrow.

We used male Calcium Calmodulin Kinase II Cre mice to delete the VAChT gene in germ-line cells by breeding them with VAChT flox mice and achieved germ line transmission. The new allele lost the VAChT gene due to Cre recombination of loxP sites, thus generating a Knockout KO allele. Heterozygous KO mice are viable and fertile. They were bred and generated homozygous KO mice that die just after birth of respiratory failure. A two-round PCR detects the mutant allele (FIG. 12, WT allele 300 bp, mutant allele 330 bp indicated by the arrow).

The foregoing is illustrative of the present invention, and is not to be construed as limiting thereof. The invention is defined by the following claims, with equivalents of the claims to be included therein.

That which is claimed is:

1. A knockout or knockdown mouse whose genome comprises a disruption in a vesicular acetylcholine transporter (VAChT) gene, said mouse having reduced expression of vesicular acetylcholine transporter protein (VAChT) therein as compared to a wild type, sex matched littermate, wherein said mouse expresses between 10 and 80 percent of VAChT as compared to said littermate as determined by western blot analysis, and wherein said mouse has increased exploration of an intruder mouse in subsequent exposures to the intruder mouse as compared to that of the wild type, sex matched littermate, which increase indicates an impairment in social recognition memory.

2. The mouse of claim 1, wherein said mouse is heterozygous for said disruption.

3. The mouse of claim 2, wherein said increased exploration is reversed upon administration of 1 mg/kg s.c. galantamine 30 minutes before presentation of the intruder mouse.

4. The mouse of claim 2, wherein said mouse has impaired performance on a repeated rotarod test as compared to the wild type sex matched littermate, which impaired performance indicates an impairment in motor learning.

5. The mouse of claim 2, wherein said mouse has increased exploration of a familiar object in an object recognition task as compared to the wild type sex matched littermate, which increased exploration indicates an impairment in object recognition memory.

6. The mouse of claim 1, wherein said mouse is homozygous for said disruption.

7. The mouse of claim 6, wherein said mouse has a decrease in frequency of miniature end-plate potentials (MEPPs) at a neuromuscular junction as compared to the wild type, sex matched littermate, which decrease indicates an impairment in neuromuscular performance.

8. The mouse of claim 6, wherein said mouse has cardiac heart failure.

9. The mouse of claim 6, wherein said mouse has decreased grip strength as compared to the wild type sex matched littermate, which decreased grip strength indicates impaired neuromuscular performance.

10. The mouse of claim 9, wherein said decreased grip strength is reversed upon administration of 1 mg/kg i.p. pyridostigmine, 1 mg/kg s.c. galantamine, or 0.3 mg/kg physostigmine.

11. The mouse of claim 1, wherein said mouse is heterozygous for said disruption and has at least a 40 percent reduction in VAChT expression as compared to the wild type, sex matched littermate.

12. The mouse of claim 1, wherein said mouse is homozygous for said disruption and has at least a 60 percent reduction in VAChT expression as compared to the wild type, sex matched littermate.

13. A cell isolated from a mouse of claim 1.

14. A cell culture produced by culturing a cell of claim 13.

15. A method of screening a compound for activity in treating an impairment in social recognition memory, comprising:

administering a test compound to a mouse of claim 1; and then detecting the presence or absence of improvement in performance in a social recognition memory test in said mouse, wherein said test measures increased exploration of an intruder mouse in subsequent exposures to the intruder mouse as compared to that of the wild type, sex matched littermate;

wherein improvement in performance of said mouse in said social recognition memory test indicates the test compound possesses said activity in treating an impairment in social recognition memory.

16. The method of claim 15, wherein said compound is a cholinesterase inhibitor.

17. A knockout or knockdown mouse whose genome comprises a disruption in a vesicular acetylcholine transporter (VAChT) gene, said mouse having reduced expression of vesicular acetylcholine transporter protein (VAChT) therein as compared to a wild type, sex matched littermate, wherein said mouse is heterozygous for said disruption and has at least a 40 percent reduction in VAChT expression as compared to the wild type, sex matched littermate, wherein said mouse has increased exploration of an intruder mouse in subsequent exposures to the intruder mouse as compared to that of the wild type, sex matched littermate, which increase indicates an impairment in social recognition memory, wherein said increased exploration can be reversed upon administration of 1 mg/kg s.c. galantamine 30 minutes before presentation of the intruder mouse, wherein said mouse has impaired performance on a repeated rotarod test, which indicates an impairment in motor learning, and wherein said mouse has increased exploration of a familiar object in an object recognition task, which increased exploration indicates an impairment in object recognition memory.

* * * * *